(12) United States Patent
Yu et al.

(10) Patent No.: US 11,338,273 B2
(45) Date of Patent: May 24, 2022

(54) MONOLITHIC CATALYST USED FOR CARBON DIOXIDE HYDROGENATION REACTION AND METHOD FOR PREPARING SAME

(71) Applicants: CHINA PETROLEUM & CHEMICAL CORPORATION, Beijing (CN); SINOPEC NANJING RESEARCH INSTITUTE OF CHEMICAL INDUSTRY CO., LTD., Jiangsu (CN)

(72) Inventors: Yang Yu, Jiangsu (CN); Haibo Chen, Jiangsu (CN); Shixin Wei, Jiangsu (CN); Yusheng Yin, Jiangsu (CN); Chunpeng Mao, Jiangsu (CN); Jiedong Tan, Jiangsu (CN); Dong Qiu, Jiangsu (CN); Tianming Xie, Jiangsu (CN); Jian He, Jiangsu (CN); Huiqin Yin, Jiangsu (CN); Xianguo Tian, Jiangsu (CN); Tianlei Dong, Jiangsu (CN); Qiong Wang, Jiangsu (CN)

(73) Assignees: CHINA PETROLEUM & CHEMICAL CORPORATION, Beijing (CN); SINOPEC NANJING RESEARCH INSTITUTE OF CHEMICAL INDUSTRY CO., LTD., Jiangsu (CN)

( * ) Notice: Subject to any disclaimer, the term of this patent is extended or adjusted under 35 U.S.C. 154(b) by 783 days.

(21) Appl. No.: 16/087,341

(22) PCT Filed: Mar. 21, 2017

(86) PCT No.: PCT/CN2017/000246
§ 371 (c)(1),
(2) Date: Sep. 21, 2018

(87) PCT Pub. No.: WO2017/161953
PCT Pub. Date: Sep. 28, 2017

(65) Prior Publication Data
US 2019/0262803 A1 Aug. 29, 2019

(30) Foreign Application Priority Data

Mar. 21, 2016 (CN) .......................... 201610159712.7
Mar. 21, 2016 (CN) .......................... 201610159715.0
(Continued)

(51) Int. Cl.
*B01J 23/80* (2006.01)
*B01J 21/04* (2006.01)
(Continued)

(52) U.S. Cl.
CPC ............... *B01J 23/80* (2013.01); *B01J 21/02* (2013.01); *B01J 21/04* (2013.01); *B01J 23/06* (2013.01);
(Continued)

(58) Field of Classification Search
CPC ... B01J 23/80; B01J 21/02; B01J 21/04; B01J 23/06; B01J 23/72; B01J 23/755;
(Continued)

(56) References Cited

U.S. PATENT DOCUMENTS

2010/0183490 A1* 7/2010 Hoke .................... B01J 37/0244
423/213.5
2015/0202572 A1* 7/2015 Chiffey .................... B01J 23/38
423/213.5

FOREIGN PATENT DOCUMENTS

CN 103127939 A 6/2013
CN 104138758 A 11/2014
(Continued)

*Primary Examiner* — James A Fiorito
(74) *Attorney, Agent, or Firm* — Novick, Kim & Lee, PLLC; Allen Xue

(57) ABSTRACT

A monolithic catalyst used for a carbon dioxide hydrogenation reaction and a method for preparing the same. The
(Continued)

catalyst comprises a carrier, a coating, and active components. The carrier is a honeycomb ceramic. The coating and the active components are separately applied to honeycomb ceramic hole walls from inside to outside. Moreover, each of the honeycomb ceramic holes is divided into an upper segment and a lower segment, and different active components are separately loaded on the two segments. The method for preparing the monolithic catalyst comprises first applying a coating to a honeycomb ceramic by means of impregnation to obtain a coating-containing carrier, and then applying active components to an upper segment and a lower segment of the coating-containing carrier successively by means of impregnation to obtain the monolithic catalyst.

27 Claims, 1 Drawing Sheet

(30) Foreign Application Priority Data

Mar. 21, 2016 (CN) .......................... 201610159716.5
Mar. 21, 2016 (CN) .......................... 201610159718.4

(51) Int. Cl.
| | | |
|---|---|---|
| *B01J 23/06* | (2006.01) | |
| *B01J 23/755* | (2006.01) | |
| *B01J 35/04* | (2006.01) | |
| *B01J 37/02* | (2006.01) | |
| *B01J 37/06* | (2006.01) | |
| *B01J 37/08* | (2006.01) | |
| *C07C 1/12* | (2006.01) | |
| *C07C 29/156* | (2006.01) | |
| *B01J 23/72* | (2006.01) | |
| *C07C 29/153* | (2006.01) | |
| *B01J 21/02* | (2006.01) | |

(52) U.S. Cl.
CPC .............. *B01J 23/72* (2013.01); *B01J 23/755* (2013.01); *B01J 35/04* (2013.01); *B01J 37/0205* (2013.01); *B01J 37/0228* (2013.01); *B01J 37/0242* (2013.01); *B01J 37/06* (2013.01); *B01J 37/08* (2013.01); *C07C 1/12* (2013.01); *C07C 29/153* (2013.01); *C07C 29/156* (2013.01); *C07C 2521/04* (2013.01); *C07C 2521/06* (2013.01); *C07C 2523/06* (2013.01); *C07C 2523/72* (2013.01); *C07C 2523/75* (2013.01); *C07C 2523/755* (2013.01); *C07C 2523/80* (2013.01)

(58) Field of Classification Search
CPC .... B01J 35/04; B01J 37/0205; B01J 37/0228; B01J 37/0242; B01J 37/06; B01J 37/08; C07C 1/12; C07C 29/153
See application file for complete search history.

(56) References Cited

FOREIGN PATENT DOCUMENTS

| | | |
|---|---|---|
| CN | 104148065 A | 11/2014 |
| EP | 2250129 A2 | 11/2010 |

* cited by examiner

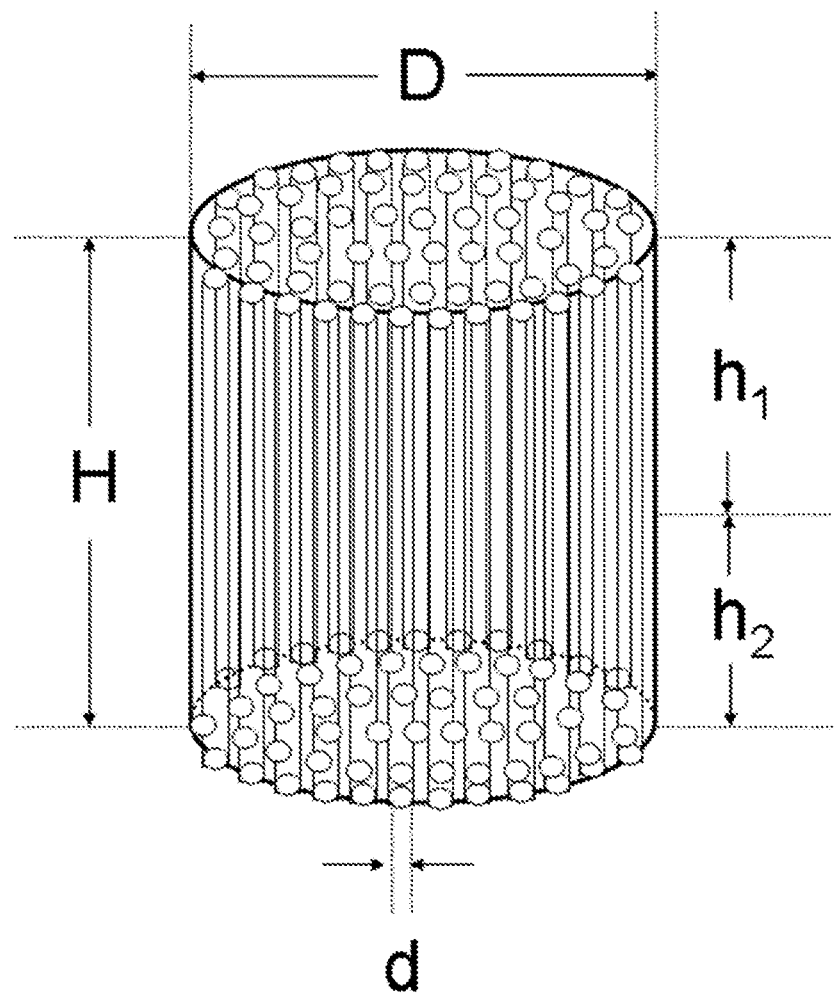

US 11,338,273 B2

MONOLITHIC CATALYST USED FOR CARBON DIOXIDE HYDROGENATION REACTION AND METHOD FOR PREPARING SAME

FIELD OF THE INVENTION

The present invention belongs to the field of catalytic technologies and particularly relates to a monolithic catalyst used for a carbon dioxide hydrogenation reaction and a method for preparing the same, more particularly a monolithic catalyst used for a carbon dioxide hydrogenation reaction for methanation or alcoholation and a method for preparing the same.

BACKGROUND OF THE INVENTION

Monolithic catalysts are new catalysts developed in recent decades and mostly have honeycomb structures. The class of catalysts is generally based on a cordierite honeycomb ceramic as a substrate, coated with a coating on its surface as a second carrier, and then loaded with active components. Monolithic catalysts usually refer to catalysts with monolithic structures having many narrow, straight or curved parallel channels. Since the cross section of the ceramic carrier catalyst developed in the early stage has a honeycomb structure, the catalyst is also called as a honeycomb-like catalyst. The basic characteristic of the class of catalysts is that there is limited radial mixing in the channels, and there is almost no mass transfer between adjacent channels.

The basic construction of the monolithic catalyst consists of three portions of a carrier, a coating and active components. The carrier not only is useful for carrying the coating and active components, but also provides a suitable fluid channel for a catalytic reaction. With regard to the coating, in general, the surface area of the monolithic catalyst carrier is very low (usually less than 1 $m^2/g$), so it is necessary to coat a coating with a high surface area on the surface of the carrier. In addition, the coating also enables the active components of the catalyst to bind effectively and firmly to the carrier, and makes the active components greatly function. At present, the coating materials of vast majority of the monolithic catalysts are $Al_2O_3$, the specific surface area of which can reach 200 $m^2/g$. They have good resistance to high temperature and chemical corrosion. Their inner holes facilitate uniform dispersion of the active components. After the monolithic carrier is applied with a coating, it needs to be embedded with active components.

During the preparation of monolithic catalysts, the coating can generally be applied to the carrier by dip-coating, sol-gel, chemical vapor deposition (CVD), in situ reaction, plasma spraying, pre-coating, electrochemical deposition, and the like. There are several methods for embedding the active components, such as impregnation, precipitation, ion exchange, in situ crystallization, and the like.

In the prior art, monolithic catalysts are an important class of catalysts involved in the catalytic purification of gaseous pollutants. They are widely used in VOC catalytic purification, industrial flue gas desulfurization, denitrification and demercuration, automobile exhaust gas purification and indoor air purification, and are rarely used in the hydrogenation reaction of carbon dioxide or carbon dioxide-enriched syngas.

CN103127939A discloses a honeycomb monolithic sulfur-tolerant methanation catalyst, which comprises: a honeycomb-like monolithic carrier prepared from a porous ceramic material and having multiple channels through the carrier; and active components loaded on the carrier, with a molybdenum oxide as a main active component and at least one of a cobalt oxide or a lanthanum oxide as a second auxiliary.

In summary, it can be seen that so far the catalysts for the carbon dioxide hydrogenation reaction in the prior art need to be improved in many aspects. Meanwhile, monolithic catalysts are rarely used for the carbon dioxide hydrogenation reaction. Moreover, even if monolithic catalysts are used, the active components on the carrier are merely single-function catalysts for a single reaction.

SUMMARY OF THE INVENTION

It is one of the objects of the present invention to provide a monolithic catalyst for a carbon dioxide hydrogenation reaction so as to solve the technical problems in the prior art such as poor catalyst activity or stability, low conversion rate of $CO_2$, and low yield of products.

It is one of the objects of the present invention to provide a monolithic catalyst for a carbon dioxide hydrogenation reaction and a method for preparing the same. The monolithic catalyst comprises a carrier, a coating, and active components. The carrier is a honeycomb ceramic. The coating and the active components are separately applied to hole walls of the honeycomb ceramic from inside to outside, characterized in that the holes of the honeycomb ceramic are divided into an upper segment and a lower segment in the longitudinal direction, and the upper segment and the lower segment respectively carry active components with different catalytic functions.

It can be seen that the present invention prepares a bifunctional catalyst from the monolithic catalyst according to a segmental supporting method, realizes an efficient conversion of carbon dioxide or carbon dioxide-enriched syngas, and combines a reverse water gas shift reaction with a synthesis reaction of lower alcohols, especially methanol, or methane. Use of the catalyst in the present invention can have a comparatively high conversion rate for carbon dioxide or carbon dioxide-enriched syngas, improve the use efficiency of the catalyst, have a good catalytic stability, reduce the reaction process, and reduce the process cost.

BRIEF DESCRIPTION OF THE DRAWING

FIG. 1 is a perspective view of the monolithic catalyst for the carbon dioxide hydrogenation reaction of the present invention, wherein D represents the cross-sectional diameter of the monolithic catalyst; H represents the length of the monolithic catalyst; d represents the hole diameter of the monolithic catalyst; $h_1$ represents the length of the upper segment of the monolithic catalyst and $h_2$ represent the length of the lower segment of the monolithic catalyst.

DETAILED DESCRIPTION OF THE INVENTION

The following detailed description of the present invention applies to various aspects of the present invention described above.

Catalyst

The present invention relates to a monolithic catalyst comprising a carrier, a coating, and active components. The carrier is a honeycomb ceramic. The coating and the active components are separately applied to hole walls of the honeycomb ceramic from inside to outside, characterized in that the holes of the honeycomb ceramic are divided into an upper segment and a lower segment in the longitudinal direction, wherein the length of the lower segment is from about ¼ to about ⅘, preferably from about ½ to about ¾, of the total length of the monolithic catalyst, and the upper segment and the lower segment respectively carry different active components.

The material of the honeycomb ceramic may be a cordierite, mullite, aluminum titanate, activated carbon, silicon carbide, activated alumina, zirconia, silicon nitride, cordierite-mullite composite matrix or cordierite-aluminum titanate composite matrix. Preferably, the material of the honeycomb ceramic is a cordierite, activated carbon, activated alumina, or cordierite-aluminum titanate composite matrix. More preferably, the material of the honeycomb ceramic is a cordierite.

The cross section of the honeycomb ceramic may be of various shapes, including rectangle, square, ellipse, circle, and the like. The specific shape can be determined according to actual conditions of the catalytic hydrogenation reaction apparatus. In a preferred embodiment of the invention, the cross section of the honeycomb ceramic is a circle. In a preferred embodiment of the invention, the honeycomb ceramic is a cylindrical cordierite. In a preferred embodiment of the invention, the honeycomb ceramic is a cylindrical cordierite, wherein the cross-sectional diameter of the cordierite is equal to the inner diameter of the hydrogenation tubular reactor.

The height of the honeycomb ceramic and the cross-sectional diameter thereof usually need to satisfy a certain proportional relationship. The specific proportional relationship can be determined according to the reaction conditions and the conditions of the reactor. In an embodiment of the invention, the ratio of the height H of the honeycomb ceramic to the cross-sectional diameter D thereof may be (about 1.5 to about 6): 1. In a preferred embodiment of the invention, the ratio of the height H of the cordierite to the cross-sectional diameter D thereof may be (about 1.5 to about 6): 1.

The cross section of the hole in the honeycomb ceramic may be triangular, square, or circular. The diameter d or side length of the cross section of the hole in the honeycomb ceramic of the present invention may be from about 1 mm to about 5 mm. In a preferred embodiment of the present invention, the honeycomb ceramic is a cylindrical cordierite. In a preferred embodiment of the invention, the inner hole of the cordierite is circular or square. In a preferred embodiment of the present invention, the diameter d or side length of the inner hole of the cordierite is from about 1 mm to about 5 mm.

The lengths of the upper segment (h1) and the lower segment (h2) of the honeycomb ceramic usually need to satisfy a certain proportion, and the specific ratio needs to be determined according to the specific catalytic reaction type. In a preferred embodiment of the present invention, the length of the lower segment (h2) of the honeycomb ceramic is preferably from about ¼ to about ⅘, more preferably from about ½ to about ¾ of the total length H of the monolithic catalyst.

The coating of the honeycomb ceramic may be an $Al_2O_3$ coating, preferably a $\gamma$-$Al_2O_3$ coating.

Active components of the upper segment of the honeycomb ceramic include Zn—Al, Cu—Zn—Al. The active components are present in form of oxides. Thus, the active components of the upper segment of the honeycomb ceramic include a combination of bimetallic oxides such as Zn—Al or a combination of polymetallic oxides such as Cu—Zn—Al. The active components of the lower segment are one of the elements of the $8^{th}$ column to the $12^{th}$ column in the periodic table or a combination thereof. The active components of the lower segment of the honeycomb ceramic include Cu, Pt, Pd, Rh, Ru, Au, Ni, Co, Fe. The active components are present in form of oxides. Thus, the active components of the lower segment of the honeycomb ceramic are preferably a combination of bimetallic oxides such as Cu—Zn, Ni—Al and the like or a combination of polymetallic oxides such as Cu—Zn—Zr, Cu—Zn—Al—Zr—Co and the like. The type of the active components, and the proportion thereof when the active components are a combination of bimetallic oxides or polymetallic oxides, both need to be determined according to the specific catalyst reaction type.

On the basis of the active components, the honeycomb ceramic may further be added with auxiliaries, the main components of which are the oxides of the elements of the $1^{st}$ to $4^{th}$ columns of the periodic table, such as alkali metal, alkaline earth metal and the like. The alkali metal is preferably Li. The alkaline earth metal is preferably Mg. It should be pointed out that in the synthesis of methanol by the carbon dioxide hydrogenation reaction, the auxiliaries are not usually an alkali metal.

The monolithic catalyst of the present invention is used for the carbon dioxide hydrogenation reaction, including the preparation of a lower alcohol, methanol and methane and the like. The lower alcohol is a C2-C5 alcohol, including the isomers thereof. The carbon dioxide hydrogenation reaction can include reacting the carbon dioxide-enriched syngas, including the preparation of methanol and the like.

In an embodiment, the active components of the upper segment of the honeycomb ceramic comprise zinc and aluminum, wherein the molar ratio of zinc to aluminum is (about 0.4-about 0.6): 1; the active components of the lower segment comprise copper, zinc, aluminum, zirconium and cobalt, wherein the molar ratio of copper, zinc, aluminum, zirconium and cobalt is 1:(about 0.8-about 1.2):(about 0.5-about 1):(about 0.5-about 1.5):(about 0.1-about 0.8). In the catalyst of the present invention, the active components are present in form of oxides. In the catalyst of the present invention, the length of the lower segment is from about ½ to about ¾ of the total length of the catalyst. The monolithic catalyst is used for carbon dioxide hydrogenation for producing a lower alcohol. The lower alcohol is a C2-C5 alcohol, including the isomers thereof.

In an embodiment, the active components of the upper segment of the honeycomb ceramic comprise zinc and aluminum, wherein the molar ratio of zinc to aluminum is (about 0.4-about 0.6): 1; the active components of the lower segment comprise copper and zinc, and the molar ratio of copper to zinc is (about 0.1-about 0.5): 1. In the catalyst of the present invention, the active components are present in form of oxides. In the catalyst of the present invention, the length of the lower segment is from about ½ to about ¾ of the total length of the catalyst. The monolithic catalyst is used for carbon dioxide hydrogenation to produce methanol.

In an embodiment, the active components of the upper segment of the honeycomb ceramic comprise zinc and aluminum, wherein the molar ratio of zinc to aluminum is (about 0.4-about 0.6):1; the active components of the lower segment comprise nickel and aluminum, and the molar ratio of nickel to aluminum is (about 0.1-about 0.5):1. In the catalyst of the present invention, the active components are present in form of oxides. In the catalyst of the present invention, the length of the lower segment is from about ½ to about ¾ of the total length of the catalyst. The monolithic catalyst is used for carbon dioxide hydrogenation to produce methane.

In an embodiment, the active components of the upper segment of the honeycomb ceramic comprise copper, zinc and aluminum, and the molar ratio of copper, zinc and aluminum is 100:(about 30-about 120):(about 10-about 50); the active components of the lower segment comprise copper, zinc and zirconium, and the molar ratio of copper, zinc and zirconium is 100:(about 30-about 120):(about 20-about 100). In the catalyst of the present invention, the active components are present in form of oxides. In the catalyst of the present invention, the length of the lower segment is from about ¼ to about ⅘ of the total length of the catalyst. The monolithic catalyst is used for the carbon dioxide-enriched syngas to produce methanol.

Preparation Method

The basic construction of the monolithic catalyst according to the present invention mainly comprises three portions of a carrier, a coating and active components. Generally, the active components are applied to the coating after application of the coating to the monolithic carrier. The coating can generally be applied to the carrier by methods such as impregnation, chemical vapor deposition (CVD), in situ reaction, electrochemical deposition, and the like. Methods of applying the active components include impregnation, precipitation, ion exchange, in situ crystallization, and the like.

In a preferred embodiment of the present invention, the coating is firstly applied to the carrier by means of impregnation to obtain a coating-containing carrier; and then two active components having different functions are respectively applied to the upper or lower segment of the coating-containing carrier by means of impregnation.

Specifically, during the application of the coating, a honeycomb ceramic is impregnated in a salt solution containing the main components of the coating for a period of time. In a preferred embodiment of the present invention, the honeycomb ceramic is impregnated in a mixed aqueous solution of aluminum nitrate and urea in an autoclave for a period of time.

The impregnation process is carried out at a certain temperature and pressure, the pressure may be from about 0.5 MPa to about 6 MPa, and the temperature may be from about 70° C. to about 150° C.

Since the impregnation process is preferably carried out under pressure, it is preferably carried out in a pressurized vessel, preferably in an autoclave. This impregnation process can be carried out for from about 1 h to about 5 h.

A precursor of a coating-containing carrier is obtained after this impregnation process. Generally the precursor also needs a heat treatment. The heat treatment is generally to firstly dry and then calcine, wherein the drying is carried out at a temperature of from about 100° C. to about 150° C., preferably about 120° C., for from about 2 h to about 5 h, preferably about 4 h, the calcination is generally carried out at a temperature of from about 600° C. to about 800° C. for from about 1 h to about 4 h, and after heat treatment, a coating-containing carrier is obtained.

The length of the lower segment of the honeycomb ceramic is from about ¼ to about ⅘, preferably from about ½ to about ¾, of the total length of the monolithic catalyst.

The order of applying different active components to the upper segment and the lower segment is not limited. The active components may be applied to the upper segment firstly and then to the lower segment; or the active components may be applied to the lower segment firstly and then to the upper segment.

In one embodiment, an active component is firstly applied to the upper segment of a coating-containing carrier. The specific process is provided as follows: the upper segment of the coating-containing carrier is firstly impregnated in a solution A for a period of time, then the upper segment is impregnated in a precipitant solution for a period of time, then after washing, a catalyst precursor 1 is obtained, and finally the catalyst precursor 1 is heat-treated to obtain a catalyst semi-finished product; then another different active component is applied to the lower segment of the catalyst semi-finished product, comprising the following specific process: the lower segment of the catalyst semi-finished product is firstly impregnated in a solution B for a period of time, then the lower segment is impregnated in the precipitant solution for a period of time, then after washing, a catalyst precursor 2 is obtained, and finally the catalyst precursor 2 is heat-treated to obtain a monolithic catalyst.

In another embodiment, an active component is firstly applied to the lower segment of the coating-containing carrier. The specific process is provided as follows: the lower segment of the coating-containing carrier is firstly impregnated in a solution B for a period of time, then the lower segment is impregnated in a precipitant solution for a period of time, then after washing, a catalyst precursor 1 is obtained, and finally the catalyst precursor 1 is heat-treated to obtain a catalyst semi-finished product; next, another different active component is applied to the upper segment of the catalyst semi-finished product, comprising the following specific process: the upper segment of the catalyst semi-finished product is firstly impregnated in the solution A for a period of time, then the upper segment is impregnated in the precipitant solution for a period of time, then after washing, a catalyst precursor 2 is obtained, and finally the catalyst precursor 2 is heat-treated to obtain a monolithic catalyst.

The solutions A and B may be solutions containing active components, which may be metal salt solutions. Specifically, the active components are various transition metals, noble metals, Group IIIA elements, or combinations thereof as described in the "Catalyst" section. In a preferred embodiment of the present invention, the solution A may be a mixed nitrate solution of zinc and aluminum, or a mixed nitrate solution of copper, zinc and aluminum. In a preferred embodiment of the present invention, the solution B may be a mixed nitrate solution of copper, zinc, aluminum, zirconium and cobalt, a mixed nitrate solution of copper and zinc, a mixed nitrate solution of nickel and aluminum, or a mixed nitrate solution of copper, zinc and zirconium.

Further, it is also possible to add some auxiliaries to the solution A or B, the main components of which are the oxides of the elements of the $1^{st}$ to $4^{th}$ columns of the periodic table, such as alkali metal, alkaline earth metal and the like. The alkali metal is preferably Li. The alkaline earth metal is preferably Mg. It should be pointed out that in the synthesis of methanol by carbon dioxide hydrogenation reaction, the auxiliaries are not generally an alkali metal.

Generally, it is also necessary to add an acid solution to the solution A or B to adjust the pH of the solutions A and B. The acid solution is generally an acid solution containing an anion portion of the salt in the solution A or B. Generally, the pH is controlled to be weakly acidic, preferably in the range of from about 6.0 to 7.0.

The type and the content of the active components and the ratio of different active components contained in the solution A or B need to be adjusted depending on the specific catalytic reaction type and reaction conditions.

In a specific embodiment, the solution A is a mixed nitrate solution of zinc and aluminum, the pH of the solution is controlled by a nitric acid solution to from about 6.0 to about 7.0, the molar ratio of zinc to aluminum is (about 0.4 to about. 0.6): 1, and the total salt molar concentration is from about 0.5 mol/L to about 2 mol/L; the solution B is a mixed nitrate solution of copper, zinc, aluminum, zirconium and cobalt, the pH of the solution is controlled by a nitric acid solution to from about 6.0 to about 7.0, the molar ratio of nitrates of copper, zinc, aluminum, zirconium and cobalt is 1:(about 0.8-about 1.2):(about 0.5-about 1):(about 0.5-about 1.5):(about 0.1-about 0.8), and the total salt molar concentration is from about 0.5 mol/L to about 1 mol/L. The monolithic catalyst produced is used for a carbon dioxide hydrogenation to produce a lower alcohol. The lower alcohol is a C2-C5 alcohol, including the isomers thereof.

In a specific embodiment, the solution A is a mixed nitrate solution of zinc and aluminum, the pH of the solution is controlled by a nitric acid solution to from about 6.0 to about 7.0, the molar ratio of zinc to aluminum is (about 0.4 to about. 0.6): 1, and the total salt molar concentration is from about 0.5 mol/L to about 2 mol/L; the solution B is a mixed nitrate solution of copper and zinc, the pH of the solution is controlled by a nitric acid solution to from about 6.0 to about 7.0, the molar ratio of copper to zinc is (about 0.1 to about 0.5): 1, and the total salt molar concentration is from about 0.5 mol/L to about 1 mol/L. The monolithic catalyst produced is used for a carbon dioxide hydrogenation to produce methanol.

In a specific embodiment, the solution A is a mixed nitrate solution of zinc and aluminum, the pH of the solution is controlled by a nitric acid solution to from about 6.0 to about 7.0, the molar ratio of zinc to aluminum is (about 0.4 to about. 0.6):1, and the total salt molar concentration is from about 0.5 mol/L to about 2 mol/L; the solution B is a mixed nitrate solution of nickel and aluminum, the pH of the solution is controlled by a nitric acid solution to from about 6.0 to about 7.0, the molar ratio of nickel to aluminum is (about 0.1 to about 0.5):1, and the total salt molar concentration is from about 0.5 mol/L to about 1 mol/L. The monolithic catalyst produced is used for a carbon dioxide hydrogenation to produce methane.

In a specific embodiment, the solution A is a mixed nitrate solution of copper, zinc and aluminum, the pH of the solution is controlled by a nitric acid solution to from about 6.0 to about 7.0, the molar ratio of copper, zinc and aluminum is 100:(about 30 to about 120):(about 10 to about 50), and the total salt molar concentration is from about 0.5 mol/L to about 2 mol/L; the solution B is a mixed nitrate solution of copper, zinc and zirconium, the pH of the solution is controlled by a nitric acid solution to from about 6.0 to about 7.0, the molar ratio of copper, zinc and zirconium is 100:(about 30 to about 120):(about 20 to about 100), and the total salt molar concentration is from about 0.5 mol/L to about 2 mol/L. The monolithic catalyst produced is used in a carbon dioxide-enriched syngas to produce methanol.

The precipitant described above is a basic salt or hydroxide, preferably an alkali metal carbonate, an alkali metal hydrogencarbonate or an alkali metal hydroxide, particularly preferably sodium carbonate, sodium hydrogencarbonate, sodium hydroxide, potassium carbonate, potassium hydrogencarbonate, potassium hydroxide or a combination thereof.

In one embodiment of the present application, the impregnation process in the solution A or solution B described above, i.e., the impregnation process in a solution containing active components, is generally carried out at a temperature above room temperature for a period of time, the temperature is generally from about 30° C. to about 80° C., and the impregnation time is from about 0.5 h to about 8 h.

The washing process for obtaining the catalyst precursor 1 or 2 may be a one-step or multi-step process, preferably a two-step washing process of washing with water firstly and then washing with anhydrous ethanol, i.e., washing with water until the conductivity is below a certain value, and then washing with anhydrous ethanol until almost no water is contained.

In a specific embodiment, the washing process is to firstly wash with water having a conductivity less than 2 μS/cm, until the conductivity of the washing liquid is less than 5 μS/cm; then to wash with anhydrous ethanol, until the water content of the washing liquid is less than 100 ppm.

After the above washing process, a heat treatment is also required. The heat treatment process at this stage may also include drying and then calcining. In one embodiment of the present application, the heat treatment described in the preparation step b or c is to firstly dry at about 90° C. for about 4 h, and then calcine at a temperature of from about 500° C. to about 800° C. for from about 0.5 h to about 4 h. In one embodiment of the present application, the heat treatment described in the preparation step b or c is to firstly dry at about 90° C. for about 4 h, and then calcine at a temperature of from about 300° C. to about 500° C. for from about 0.5 h to about 4 h. In one embodiment of the present application, the heat treatment described in the preparation step b or c is to firstly dry at about 90° C. for about 4 h, and then calcine at a temperature of from about 300° C. to about 400° C. for from about 0.5 h to about 4 h.

Use

The monolithic catalyst of the present invention can be used in a carbon dioxide hydrogenation reaction, including but not limited to various types of carbon dioxide hydrogenations for methanation or alcoholation reaction, such as a reaction of $CO_2$ hydrogenation for producing a lower alcohol, a reaction of $CO_2$ hydrogenation for producing methanol, a reaction of $CO_2$ hydrogenation for producing methane, and a reaction of a $CO_2$-enriched syngas for producing methanol, and the like.

In the carbon dioxide hydrogenation reaction, the hydrogen source may be hydrogen or syngas, etc. When syngas is used as a hydrogen source, carbon monoxide in the syngas can be converted to, for example, methanol and the like, in the lower segment of the monolithic catalyst of the present invention. In a specific embodiment of the present invention, the monolithic catalyst of the present invention is used in a reaction for producing methanol from a $CO_2$-enriched syngas.

In a specific embodiment, the monolithic catalyst of the present invention is a monolithic catalyst for $CO_2$ hydrogenation for producing a lower alcohol, which monolithic catalyst is obtained by the following preparation steps:

a. immersing a honeycomb ceramic in a mixed aqueous solution of aluminum nitrate and urea in an autoclave for treatment to obtain a precursor of a coating-containing carrier, and heat-treating the precursor to obtain a coating-containing carrier;

b. firstly impregnating the upper segment of the coating-containing carrier resultant from step a in a mixed nitrate solution of zinc and aluminum, then impregnating the upper segment in a precipitant solution, then after washing, obtaining a catalyst precursor 1, and heat-treating the catalyst precursor 1 to obtain a catalyst semi-finished product;

c. firstly impregnating the lower segment of the catalyst semi-finished product from step b in a mixed nitrate solution of copper, zinc, aluminum, zirconium and cobalt, then impregnating the lower segment in the precipitant solution, then after washing, obtaining a catalyst precursor 2, and heat-treating the catalyst precursor 2 to obtain a monolithic catalyst;

the length h2 of the lower segment being from about ½ to about ¾ of the total length H of the monolithic catalyst.

The order of the above steps b and c may be changed. That is, firstly impregnating the lower segment of the coating-containing carrier resultant from step a in a mixed nitrate solution of copper, zinc, aluminum, zirconium and cobalt, then impregnating the lower segment in the precipitant solution, then after washing, obtaining a catalyst precursor 1, and heat-treating the catalyst precursor 1 to obtain a catalyst semi-finished product; then, firstly impregnating the upper segment of the resultant catalyst semi-finished product in a mixed nitrate solution of zinc and aluminum, and then impregnating the upper segment in the precipitant solution, then after washing, obtaining a catalyst precursor 2, and heat-treating the catalyst precursor 2 to obtain a monolithic catalyst.

The lower alcohol is a C2-C5 alcohol, including the isomers thereof.

The honeycomb ceramic in the preparation step a is a cylindrical cordierite having a cross-sectional diameter equal to the inner diameter of a tubular reactor for the production of methanol with a $CO_2$-enriched syngas. The ratio of the height H of the cordierite to the cross-sectional diameter D thereof is (about 1.5 to about 6):1. The inner hole diameter d of the cordierite is from about 1 mm to about 5 mm.

The treatment in the preparation step a is carried out in an autoclave at a treatment pressure of from about 0.5 MPa to about 6 Mpa and a treatment temperature of from about 70° C. to about 150° C. for a treatment period of from about 1 h to about 5 h.

The heat treatment in the preparation step a is to firstly dry at about 120° C. for about 4 h, and then calcine at from about 600° C. to about 800° C. for from about 1 h to about 4 h.

The pH of the mixed nitrate solution of zinc and aluminum in the preparation step b is controlled to from about 6.0 to about 7.0; the molar ratio of zinc to aluminum is (about 0.4 to about 0.6):1; the total salt molar concentration is from about 0.5 mol/L to about 2 mol/L.

The pH of the mixed nitrate solution of copper, zinc, aluminum, zirconium and cobalt in the preparation step c is controlled to from about 6.0 to about 7.0; the molar ratio of nitrates of copper, zinc, aluminum, zirconium and cobalt is 1:(about 0.8-about 1.2):(about 0.5-about 1):(about 0.5-about 1.5):(about 0.1-about 0.8); the total salt molar concentration is from about 0.5 mol/L to about 1 mol/L.

The precipitant in the preparation step b or c is one of sodium carbonate, sodium hydrogencarbonate, sodium hydroxide, potassium carbonate, potassium hydrogencarbonate and potassium hydroxide.

The temperature of the impregnation in the preparation step b or c is from about 30° C. to about 80° C.; the impregnation time is from about 0.5 h to about 8 h.

The washing in the preparation step b or c is to firstly wash with water having a conductivity less than 2 μS/cm, until the conductivity of the washing liquid is less than 5 μS/cm; then to wash with anhydrous ethanol, until the water content of the washing liquid is less than 100 ppm.

The heat treatment in the preparation step b or c is to firstly dry at about 90° C. for about 4 h, and then calcine at from about 500° C. to about 800° C. for from about 0.5 h to about 4 h.

The monolithic catalyst prepared by such a method can significantly improve the conversion rate of $CO_2$, the selectivity of $C_{2+}$ alcohol and isobutanol in the reaction of $CO_2$ hydrogenation for producing a lower alcohol. The preparation method is simple and is easy for industrial applications.

In a specific embodiment, the monolithic catalyst of the present invention is a monolithic catalyst for $CO_2$ hydrogenation for producing methanol, which monolithic catalyst is obtained by the following preparation steps:

a. immersing a honeycomb ceramic in a mixed aqueous solution of aluminum nitrate and urea in an autoclave for treatment to obtain a precursor of a coating-containing carrier, and heat-treating the precursor to obtain a coating-containing carrier;

b. firstly impregnating the upper segment of the coating-containing carrier resultant from step a in a mixed nitrate solution of zinc and aluminum, and then impregnating the upper segment in a precipitant solution, then after washing, obtaining a catalyst precursor 1, and heat-treating the catalyst precursor 1 to obtain a catalyst semi-finished product;

c. firstly impregnating the lower segment of the catalyst semi-finished product resultant from step b in a mixed nitrate solution of copper and zinc, then impregnating the lower segment in the precipitant solution, then after washing, obtaining a catalyst precursor 2, and heat-treating the catalyst precursor 2 to obtain a monolithic catalyst;

the length h2 of the lower segment being from about ½ to about ¾ of the total length H of the monolithic catalyst.

The order of the above steps b and c may be changed. That is, firstly impregnating the lower segment of the coating-containing carrier resultant from step a in a mixed nitrate solution of copper and zinc, then impregnating the lower segment in the precipitant solution, then after washing, obtaining a catalyst precursor 1, and heat-treating the catalyst precursor 1 to obtain a catalyst semi-finished product; then firstly impregnating the upper segment of the resultant catalyst semi-finished product in a mixed nitrate solution of zinc and aluminum, then impregnating the upper segment in the precipitant solution, then after washing, obtaining a catalyst precursor 2, and heat-treating the catalyst precursor 2 to obtain a monolithic catalyst.

The honeycomb ceramic in the preparation step a is a cylindrical cordierite having a cross-sectional diameter equal to the inner diameter of a tubular reactor for the production of methanol by $CO_2$ hydrogenation, The ratio of the height H of the cordierite to the cross-sectional diameter D thereof is (about 1.5 to about 6): 1. The diameter d of the inner hole of the cordierite is from about 1 mm to about 5 mm.

The treatment in the preparation step a is carried out in an autoclave at a treatment pressure of from about 0.5 MPa to about 6 Mpa and a treatment temperature of from about 70° C. to about 150° C. for a treatment period of from about 1 h to about 5 h.

The heat treatment in the preparation step a is to firstly dry at about 120° C. for about 4 h, and then calcine at from about 600° C. to about 800° C. for from about 1 h to about 4 h.

The pH of the mixed nitrate solution of zinc and aluminum in the preparation step b is controlled to from about 6.0 to about 7.0; the molar ratio of zinc to aluminum is (about 0.4 to about 0.6):1; the total salt molar concentration is from about 0.5 mol/L to about 2 mol/L.

The pH of the mixed nitrate solution of copper and zinc in the preparation step c is controlled to from about 6.0 to about 7.0; the molar ratio of copper to zinc is (about 0.1 to about 0.5):1; the total salt molar concentration is from about 0.5 mol/L to about 1 mol/L.

The precipitant in the preparation step b or c is one of sodium carbonate, sodium hydrogencarbonate, sodium hydroxide, potassium carbonate, potassium hydrogencarbonate and potassium hydroxide.

The temperature of the impregnation in the preparation step b or c is from about 30° C. to about 80° C.; and the impregnation time is from about 0.5 h to about 8 h.

The washing in the preparation step b or c is to firstly wash with water having a conductivity of less than 2 μS/cm, until the washing liquid has a conductivity less than 5 μS/cm; then to wash with anhydrous ethanol, until the washing liquid has a water content less than 100 ppm.

The heat treatment in the preparation step b or c is to firstly dry at about 90° C. for about 4 h, and then calcine at from about 500° C. to about 800° C. for from about 0.5 h to about 4 h.

The monolithic catalyst prepared by such a method can significantly improve the conversion rate of $CO_2$ and the hydrothermal stability of catalyst in the reaction of $CO_2$ hydrogenation for producing methanol. The preparation method is simple and is easy for industrial applications.

In a specific embodiment, the monolithic catalyst of the present invention is a monolithic catalyst for $CO_2$ hydrogenation for producing methane, which monolithic catalyst is obtained by the following preparation steps:

a. immersing a honeycomb ceramic in a mixed aqueous solution of aluminum nitrate and urea in an autoclave for treatment to obtain a precursor of a coating-containing carrier, and heat-treating the precursor to obtain a coating-containing carrier;

b. firstly impregnating the upper segment of the coating-containing carrier resultant from step a in a mixed nitrate solution of zinc and aluminum, then impregnating the upper segment in a precipitant solution, then after washing, obtaining a catalyst precursor 1, and heat-treating the catalyst precursor 1 to obtain a catalyst semi-finished product;

c. firstly impregnating the lower segment of the catalyst semi-finished product resultant from step b in a mixed nitrate solution of nickel and aluminum, then impregnating the lower segment in the precipitant solution, then after washing, obtaining a catalyst precursor 2, and heat-treating the catalyst precursor 2 to obtain a monolithic catalyst;

the length h2 of the lower segment being from about ½ to about ¾ of the total length H of the monolithic catalyst.

The order of the above steps b and c may be changed. That is, firstly impregnating the lower segment of the coating-containing carrier resultant from step a in a mixed nitrate solution of nickel and aluminum, and then impregnating the lower segment in the precipitant solution, after washing, obtaining a catalyst precursor 1, and heat-treating the catalyst precursor 1 to obtain a catalyst semi-finished product; then firstly impregnating the upper segment of the resultant catalyst semi-finished product in a mixed nitrate solution of zinc and aluminum, then impregnating the upper segment in the precipitant solution, then after washing, obtaining a catalyst precursor 2, and heat-treating the catalyst precursor 2 to obtain a monolithic catalyst.

The honeycomb ceramic in the preparation step a is a cylindrical cordierite having a cross-sectional diameter equal to the inner diameter of a tubular reactor for the production of methanol by $CO_2$-enriched syngas. The ratio of the height H of the cordierite to the cross-sectional diameter D thereof is (about 1.5 to about 6):1. The diameter d of the inner hole of the cordierite is from about 1 mm to about 5 mm.

The treatment in the preparation step a is carried out in an autoclave at a treatment pressure of from about 0.5 MPa to about 6 Mpa and a treatment temperature of from about 70° C. to about 150° C. for a treatment period of from about 1 h to about 5 h.

The heat treatment in the preparation step a is to firstly dry at about 120° C. for about 4 h, and then calcine at from about 600° C. to about 800° C. for from about 1 h to about 4 h.

The pH of the mixed nitrate solution of zinc and aluminum in the preparation step b is controlled to from about 6.0 to about 7.0; the molar ratio of zinc to aluminum is (about 0.4 to about 0.6):1; the total salt molar concentration is from about 0.5 mol/L to about 2 mol/L.

The pH of the mixed nitrate solution of nickel and aluminum in the preparation step c is controlled to from about 6.0 to about 7.0; the molar ratio of nickel to aluminum is (about 0.1 to about 0.5):1; the total salt molar concentration is from about 0.5 mol/L to about 1 mol/L.

The precipitant in the preparation step b or c is one of sodium carbonate, sodium hydrogencarbonate, sodium hydroxide, potassium carbonate, potassium hydrogencarbonate and potassium hydroxide.

The temperature of the impregnation in the preparation step b or c is from about 30° C. to about 80° C.; and the impregnation time is from about 0.5 h to about 8 h.

The washing in the preparation step b or c is to firstly wash with water having a conductivity of less than 2 μS/cm, until the washing liquid has a conductivity less than 5 μS/cm; then to wash with anhydrous ethanol, until the washing liquid has a water content less than 100 ppm.

The heat treatment in the preparation step b or c is to firstly dry at about 90° C. for about 4 h, and then calcine at from about 500° C. to about 800° C. for from about 0.5 h to about 4 h.

The monolithic catalyst prepared by such a method can significantly improve the conversion rate of $CO_2$ and the methane content in the product gas in the reaction of $CO_2$ hydrogenation for producing methane, and meanwhile, can effectively reduce the carbon deposition rate of catalyst upon long-term running. The preparation method is simple and is easy for industrial applications.

In a specific embodiment, the monolithic catalyst of the present invention is a monolithic catalyst for using $CO_2$-enriched syngas to produce methanol, which monolithic catalyst is obtained by the following preparation steps:

a. immersing a honeycomb ceramic in a mixed aqueous solution of aluminum nitrate and urea in an autoclave for treatment to obtain a precursor of a coating-containing carrier, and heat-treating the precursor to obtain a carrier;

b. firstly impregnating the upper segment of the coating-containing carrier resultant from step a in a mixed nitrate solution of copper, zinc and aluminum, then impregnating the upper segment in a precipitant solution, then after washing, obtaining a catalyst precursor 1, and heat-treating the catalyst precursor 1 to obtain a catalyst semi-finished product;

c. firstly impregnating the lower segment of the catalyst semi-finished product resultant from step b in a mixed nitrate solution of copper, zinc and zirconium, then impregnating the lower segment in the precipitant solution, then after washing, obtaining a catalyst precursor 2, and heat-treating the catalyst precursor 2 to obtain a monolithic catalyst.

The sum of the upper segment length h1 and the lower segment length h2 is equal to the total length H of the monolithic catalyst; the ratio of the upper segment length h1 to the lower segment length h2 is (about ¼ to about 3): 1. The length h2 of the lower segment is about ¼ to about ⅘ of the total length H of the monolithic catalyst.

The order of the above steps b and c may be changed. That is, firstly impregnating the lower segment of the coating-containing carrier resultant from step a in a mixed nitrate solution of copper, zinc and zirconium, then impregnating the lower segment in the precipitant solution, then after washing, obtaining a catalyst precursor 1, and heat-treating the catalyst precursor 1 to obtain a catalyst semi-finished product; then firstly impregnating the upper segment of the resultant catalyst semi-finished product in a mixed nitrate solution of copper, zinc and aluminum, then impregnating the upper segment in the precipitant solution, then after washing, obtaining a catalyst precursor 2, and heat-treating the catalyst precursor 2 to obtain a monolithic catalyst.

In general, the honeycomb ceramic is a cylindrical cordierite having a cross-sectional diameter equal to the inner diameter of a tubular reactor for the production of methanol by $CO_2$-enriched syngas. The ratio of the height H of the cordierite to the cross-sectional diameter D thereof is about 1.5 to about 6. The diameter d of the inner hole of the cordierite is from about 1 mm to about 5 mm.

The treatment in the preparation step a is carried out in an autoclave at a treatment pressure of from about 0.5 MPa to about 6 Mpa and a treatment temperature of from about 70° C. to about 150° C. for a treatment period of from about 1 h to about 5 h.

The heat treatment in the preparation step a is to firstly dry at about 120° C. for about 4 h, and then calcine at from about 600° C. to about 800° C. for from about 1 h to about 4 h.

The pH of the mixed nitrate solution of copper, zinc and aluminum in the preparation step b is controlled to from about 6.0 to about 7.0; the molar ratio of copper, zinc and aluminum is 100:(about 30 to about 120):(about 10 to about 50); the total salt molar concentration is from about 0.5 mol/L to about 2 mol/L.

The pH of the mixed nitrate solution of copper, zinc and zirconium in the preparation step c is controlled to from about 6.0 to about 7.0; the molar ratio of copper, zinc and zirconium is 100:(about 30 to about 120):(about 20 to about 100); the total salt molar concentration is from about 0.5 mol/L to about 2 mol/L.

The precipitant in the preparation step b or c is one of sodium carbonate, sodium hydrogencarbonate, sodium hydroxide, potassium carbonate, potassium hydrogencarbonate and potassium hydroxide.

The temperature of the nitrate solution for impregnation in the preparation step b or c is from about 30° C. to about 80° C.; and the impregnation time is from about 0.5 h to about 8 h.

The washing in the preparation step b or c is to firstly wash with water having a conductivity of less than 2 µS/cm, until the washing liquid has a conductivity less than 5 µS/cm; then to wash with anhydrous ethanol, until the washing liquid has a water content less than 100 ppm.

The heat treatment in the preparation step b or c is to firstly dry at about 90° C. for about 4 h, and then calcine at from about 300° C. to about 500° C. for from about 0.5 h to about 4 h.

The monolithic catalyst prepared by such a method is a bifunctional catalyst, and can significantly improve the conversion rates of CO and $CO_2$ in the reaction for the production of methanol by $CO_2$-enriched syngas and the stability of catalyst.

EXAMPLES

The following examples are used to further illustrate the present invention, but are not intended to limit the present invention.

The characterization method of the coating and the active components of the monolithic catalyst of the present invention is:

(1) XPS characterization (qualitative and quantitative analysis of the compositional elements of the active components)

X-ray photoelectron spectroscopy (U.K. Thermo ESCALAB 250 Xi) uses single-color Al Kα (1486.6 eV) as the excitation light source; the sample is tableted and vacuumed (the vacuum degree is higher than $5\times10^{0.8}$ Pa); the spectrum is collected at room temperature; the surface-contaminated carbon C1s=284.6 eV is used as the internal standard to calibrate the charge effect on the surface of the sample.

(2) XRF characterization (qualitative and quantitative analysis of the compositional elements of the coating)

X-ray fluorescence spectrum (Japan Rigaku, model: ZSX-Primus), end window rhodium palladium, voltage 30-60 kV, current 30-60 mA, wide slit, diaphragm aperture 20 mm.

According to the tests with the apparatuses as described above, the characterization analysis results show that the active components and coatings of the monolithic catalysts of the following examples have the uniform compositions.

Example 1

A cylindrical cordierite with a cross-sectional diameter of 135 mm, a height of 52.5 mm and an inner hole diameter of 1 mm was immersed in an aqueous solution of aluminum nitrate and urea in an autoclave for treatment (the amount-of-substance ratio of aluminum nitrate to urea was 1.2, and the amount-of-substance concentration of aluminum nitrate was 1 mol/L) at a pressure of 0.5 MPa, at a temperature of 150° C. and for a period of 5 h to obtain a precursor of a coating-containing carrier; the precursor was dried in air at 120° C. for 4 h and calcined at 600° C. for 4 h to obtain a coating-containing carrier.

37.8 g of zinc nitrate and 106.5 g of aluminum nitrate were dissolved in 1400 mL of deionized water to prepare a mixed solution of zinc and aluminum. A suitable amount of nitric acid was added to control the solution to have a pH of 6.0. The upper segment of the above-mentioned coating-containing carrier (½ of the total height) was impregnated in the mixed solution of zinc and aluminum at 30° C. for 8 h. Then, said upper segment was impregnated in a 30° C., 1 mol/L sodium carbonate solution for 10 min, then washed with water having a conductivity less than 2 µS/cm, until the conductivity of the washing liquid was less than 5 µS/cm; then it was washed with anhydrous ethanol, till the water content in the washing liquid was less than 100 ppm; thereafter, it was dried in a drying oven at 90° C. for 4 h, and calcined in air at 500° C. for 4 h to obtain a catalyst semi-finished product.

47 g of copper nitrate, 37.8 g of zinc nitrate, 26.625 g of aluminum nitrate, 39.875 g of zirconium nitrate and 4.575 g of cobalt nitrate were dissolved in 1450 mL of deionized water to prepare a mixed nitrate solution of copper, zinc, aluminum, zirconium and cobalt. A suitable amount of nitric acid was added to control the solution to have a pH of 6.0. The lower segment of the above-mentioned coating-containing carrier (½ of the total height) was impregnated in the mixed nitrate solution of copper, zinc, aluminum, zirconium and cobalt at 30° C. for 8 h. Then, said lower segment was impregnated in a 30° C., 1 mol/L sodium carbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 4 h to obtain a monolithic catalyst y1.

Example 2

A cylindrical cordierite with a cross-sectional diameter of Φ35 mm, a height of 63 mm and an inner hole diameter of 2 mm was immersed in an aqueous solution of aluminum nitrate and urea in an autoclave for treatment (the amount-of-substance ratio of aluminum nitrate to urea was 1.8, and the amount-of-substance concentration of aluminum nitrate was 1 mol/L) at a pressure of 1 MPa, at a temperature of 120° C. and for a period of 4 h to obtain a precursor of a coating-containing carrier; the precursor was dried in air at 120° C. for 4 h and calcined at 600° C. for 4 h to obtain a coating-containing carrier.

47.25 g of zinc nitrate and 106.7 g of aluminum nitrate were dissolved in 750 mL of deionized water to prepare a mixed solution of zinc and aluminum. A small amount of nitric acid was added to control the solution to have a pH of 6.5. The upper segment of the above-mentioned coating-containing carrier (9/20 of the total height) was impregnated in the mixed solution of zinc and aluminum at 50° C. for 7 h. Then, said upper segment was impregnated in a 50° C., 1 mol/L sodium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 600° C. for 3 h to obtain a one-time impregnation sample. Then, the aforesaid process of mixed solution impregnation-sodium hydrogencarbonate solution impregnation-washing-drying-calcination was repeated once to obtain a catalyst semi-finished product.

47 g of copper nitrate, 47.25 g of zinc nitrate, 42.6 g of aluminum nitrate, 63.8 g of zirconium nitrate and 13.725 g of cobalt nitrate were dissolved in 1220 mL of deionized water to prepare a mixed nitrate solution of copper, zinc, aluminum, zirconium and cobalt. A small amount of nitric acid was added to control the solution to have a pH of 6.5. The lower segment of the above-mentioned coating-containing carrier (11/20 of the total height) was impregnated in the mixed nitrate solution of copper, zinc, aluminum, zirconium and cobalt at 50° C. for 7 h. Then, said lower segment was impregnated in a 50° C., 1 mol/L sodium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 600° C. for 4 h to obtain a one-time impregnation sample. Then, the aforesaid process of mixed solution impregnation-sodium hydrogencarbonate solution impregnation-washing-drying-calcination was repeated once to obtain a monolithic catalyst y2.

Example 3

A cylindrical cordierite with a cross-sectional diameter of Φ35 mm, a height of 70 mm and an inner hole diameter of 3 mm was immersed in an aqueous solution of aluminum nitrate and urea in an autoclave for treatment (the amount-of-substance ratio of aluminum nitrate to urea was 2, and the amount-of-substance concentration of aluminum nitrate was 1 mol/L) at a pressure of 2 MPa, at a temperature of 100° C. and for a period of 4 h to obtain a precursor of a coating-containing carrier; the precursor was dried in air at 120° C. for 4 h and calcined at 700° C. for 3 h to obtain a coating-containing carrier.

28.35 g of zinc nitrate and 53.25 g of aluminum nitrate were dissolved in 310 mL of deionized water to prepare a mixed solution of zinc and aluminum having a pH of 7.0. The upper segment of the above-mentioned coating-containing carrier (3/8 of the total height) was impregnated in the mixed solution of zinc and aluminum at 60° C. for 5 h. Then, said upper segment was impregnated in a 60° C., 1 mol/L potassium carbonate solution for 10 min, then washed with water having a conductivity less than 2 S/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 700° C. for 1 h to obtain a one-time impregnation sample. Then, the aforesaid process of mixed solution impregnation-potassium carbonate solution impregnation-washing-drying-calcination was repeated twice to obtain a catalyst semi-finished product.

47 g of copper nitrate, 56.7 g of zinc nitrate, 53.25 g of aluminum nitrate, 63.8 g of zirconium nitrate and 36.6 g of cobalt nitrate were dissolved in 1250 mL of deionized water to prepare a mixed nitrate solution of copper, zinc, aluminum, zirconium and cobalt having a pH of 7.0. The lower segment of the above-mentioned coating-containing carrier (5/8 of the total height) was impregnated in the mixed nitrate solution of copper, zinc, aluminum, zirconium and cobalt at 60° C. for 5 h. Then, said lower segment was impregnated in a 60° C., 1 mol/L potassium carbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 1 h to obtain a one-time impregnation sample. Then, the aforesaid process of mixed solution impregnation-potassium carbonate solution impregnation-washing-drying-calcination was repeated twice to obtain a monolithic catalyst y3.

Example 4

A cylindrical cordierite with a cross-sectional diameter of 135 mm, a height of 105 mm and an inner hole diameter of 3 mm was immersed in an aqueous solution of aluminum nitrate and urea in an autoclave for treatment (the amount-of-substance ratio of aluminum nitrate to urea was 2.5, and the amount-of-substance concentration of aluminum nitrate was 1 mol/L) at a pressure of 3 MPa, at a temperature of 70° C. and for a period of 3 h to obtain a precursor of a coating-containing carrier; the precursor was dried in air at 120° C. for 4 h and calcined at 750° C. for 2 h to obtain a coating-containing carrier.

56.7 g of zinc nitrate and 106.4 g of aluminum nitrate were dissolved in 400 mL of deionized water to prepare a mixed solution of zinc and aluminum. A small amount of nitric acid was added to control the solution to have a pH of 6.5. The upper segment of the above-mentioned coating-containing carrier (½ of the total height) was impregnated in the mixed solution of zinc and aluminum at 70° C. for 3 h. Then, said upper segment was impregnated in a 70° C., 1 mol/L potassium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 800° C. for 0.5 h to obtain a one-time impregnation sample. Then, the aforesaid process of mixed solution impregnation-potassium hydrogencarbonate solution impregnation-washing-drying-calcination was repeated twice to obtain a catalyst semi-finished product.

47 g of copper nitrate, 37.8 g of zinc nitrate, 53.25 g of aluminum nitrate, 79.75 g of zirconium nitrate and 22.875 g of cobalt nitrate were dissolved in 2150 mL of deionized water to prepare a mixed nitrate solution of copper, zinc, aluminum, zirconium and cobalt. A small amount of nitric acid was added to control the solution to have a pH of 6.5. The lower segment of the above-mentioned coating-containing carrier (½ of the total height) was impregnated in the mixed nitrate solution of copper, zinc, aluminum, zirconium and cobalt at 70° C. for 3 h. Then, said lower segment was impregnated in a 70° C., 1 mol/L potassium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 2 h to obtain a one-time impregnation sample. Then, the aforesaid process of mixed solution impregnation-potassium hydrogencarbonate solution impregnation-washing-drying-calcination was repeated twice to obtain a monolithic catalyst y4.

Example 5

A cylindrical cordierite with a cross-sectional diameter of 135 mm, a height of 105 mm and an inner hole diameter of 3 mm was immersed in an aqueous solution of aluminum nitrate and urea in an autoclave for treatment (the amount-of-substance ratio of aluminum nitrate to urea was 3, and the amount-of-substance concentration of aluminum nitrate was 1 mol/L) at a pressure of 4 MPa, at a temperature of 100° C. and for a period of 1 h to obtain a precursor of a coating-containing carrier; the precursor was dried in air at 120° C. for 4 h and calcined at 800° C. for 1 h to obtain a coating-containing carrier.

37.8 g of zinc nitrate and 106.5 g of aluminum nitrate were dissolved in 700 mL of deionized water to prepare a mixed solution of zinc and aluminum. A small amount of nitric acid was added to control the solution to have a pH of 6.5. The upper segment of the above-mentioned coating-containing carrier (7/20 of the total height) was impregnated in the mixed solution of zinc and aluminum at 80° C. for 0.5 h. Then, said upper segment was impregnated in a 80° C., 1 mol/L sodium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 800° C. for 0.5 h to obtain a one-time impregnation sample. Then, the aforesaid process of mixed solution impregnation-sodium hydroxide solution impregnation-washing-drying-calcination was repeated twice to obtain a catalyst semi-finished product.

47 g of copper nitrate, 33.075 g of zinc nitrate, 37.275 g of aluminum nitrate, 79.75 g of zirconium nitrate and 22.875 g of cobalt nitrate were dissolved in 1950 mL of deionized water to prepare a mixed nitrate solution of copper, zinc, aluminum, zirconium and cobalt. A small amount of nitric acid was added to control the solution to have a pH of 6.5. The lower segment of the above-mentioned coating-containing carrier (13/20 of the total height) was impregnated in the mixed nitrate solution of copper, zinc, aluminum, zirconium and cobalt at 80° C. for 0.5 h. Then, said lower segment was impregnated in a 80° C., 1 mol/L sodium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 2 h to obtain a one-time impregnation sample. Then, the aforesaid process of mixed solution impregnation-sodium hydroxide solution impregnation-washing-drying-calcination was repeated twice to obtain a monolithic catalyst y5.

Example 6

A cylindrical cordierite with a cross-sectional diameter of Φ35 mm, a height of 210 mm and an inner hole diameter of 5 mm was immersed in an aqueous solution of aluminum nitrate and urea in an autoclave for treatment (the amount-of-substance ratio of aluminum nitrate to urea was 3.5, and the amount-of-substance concentration of aluminum nitrate was 1 mol/L) at a pressure of 6 MPa, at a temperature of 80° C. and for a period of 1 h to obtain a precursor of a coating-containing carrier; the precursor was dried in air at 120° C. for 4 h and calcined at 650° C. for 2 h to obtain a coating-containing carrier.

37.8 g of zinc nitrate and 106.5 g of aluminum nitrate were dissolved in 700 mL of deionized water to prepare a mixed solution of zinc and aluminum. A small amount of nitric acid was added to control the solution to have a pH of 6.5. The upper segment of the above-mentioned coating-containing carrier (¼ of the total height) was impregnated in the mixed solution of zinc and aluminum at 50° C. for 1 h. Then, said upper segment was impregnated in a 50° C., 1 mol/L potassium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 800° C. for 0.5 h to obtain a one-time impregnation sample. Then, the aforesaid process of mixed solution impregnation-potassium hydroxide solution impregnation-washing-drying-calcination was repeated twice to obtain a catalyst semi-finished product.

47 g of copper nitrate, 33.075 g of zinc nitrate, 119.625 g of aluminum nitrate, 36.6 g of zirconium nitrate and 22.875 g of cobalt nitrate were dissolved in 2350 mL of deionized water to prepare a mixed nitrate solution of copper, zinc, aluminum, zirconium and cobalt. A small amount of nitric acid was added to control the solution to have a pH of 6.5. The lower segment of the above-mentioned coating-containing carrier (¾ of the total height) was impregnated in the mixed nitrate solution of copper, zinc, aluminum, zirconium and cobalt at 50° C. for 0.5 h. Then, said lower segment was impregnated in a 50° C., 1 mol/L potassium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 1 h to obtain a one-time impregnation sample. Then, the aforesaid process of mixed solution impregnation-potassium hydroxide solution impregnation-washing-drying-calcination was repeated twice to obtain a monolithic catalyst y6.

Comparative Example 1

47 g of copper nitrate, 33.075 g of zinc nitrate, 37.325 g of aluminum nitrate, 79.75 g of zirconium nitrate and 22.875 g of cobalt nitrate were dissolved in 2000 mL of deionized water to obtain a mixed nitrate solution, and the solution was preheated to 80° C.; 1 mol/L sodium carbonate aqueous solution was formulated and preheated to 80° C.; the mixed nitrate solution and sodium carbonate solution were concurrently added to 300 mL of 80° C. deionized water with the pH maintained to 7.2, and then aged in situ for 1 h; the filtration was carried out, and the deionized water having a conductivity less than 2 S/cm was used for suction filtration and washing of filter cake, until the conductivity of filter liquor was less than 5 μS/cm; ethanol was then used for suction filtration and washing, till the water content in the filter cake was less than 100 ppm, thereby obtaining a catalyst precursor; the precursor was dried in a drying oven at 90° C. for 4 h, and calcined in air at 500° C. for 2 h; the resulting powder was tabletted and shaped into a cylinder (Φ5 mm×5 mm) to obtain a catalyst C1.

Comparative Example 2

A cylindrical cordierite with a cross-sectional diameter of 135 mm, a height of 210 mm and an inner hole diameter of 5 mm was immersed in an aqueous solution of aluminum nitrate and urea in an autoclave for treatment (the amount-of-substance ratio of aluminum nitrate to urea was 3.5, and the amount-of-substance concentration of aluminum nitrate was 1 mol/L) at a pressure of 6 MPa, at a temperature of 80° C. and for a period of 1 h to obtain a precursor of a coating-containing carrier; the precursor was dried in air at 120° C. for 4 h and calcined at 650° C. for 2 h to obtain a coating-containing carrier.

47 g of copper nitrate, 33.075 g of zinc nitrate, 37.325 g of aluminum nitrate, 79.75 g of zirconium nitrate and 22.875 g of cobalt nitrate were dissolved in 2000 mL of deionized water to prepare a mixed nitrate solution of copper, zinc, aluminum, zirconium and cobalt. A small amount of nitric acid was added to control the solution to have a pH of 6.5. The above-mentioned coating-containing carrier was firstly impregnated in the mixed nitrate solution at 80° C. for 1 h. Then, said coating-containing carrier was impregnated in a 80° C., 1 mol/L sodium hydroxide solution for 10 min, then washed with water having a conductivity less than 2 μS/cm, until the conductivity of the washing liquid was less than 5 S/cm; then it was washed with anhydrous ethanol, till the water content in the washing liquid was less than 100 ppm; thereafter, it was dried in a drying oven at 90° C. for 4 h, and calcined in air at 500° C. for 2 h to obtain a one-time impregnation sample. Then, the aforesaid process of mixed solution impregnation-potassium hydroxide solution impregnation-washing-drying-calcination was repeated twice to obtain a monolithic catalyst U2.

Activity test conditions: the activity of the catalyst was evaluated on a fixed bed isothermal reactor, and the reaction tube had an inner diameter of 35 mm and a length of 1200 mm. The catalyst was subjected to in situ reduction in a reactor with a $H_2/N_2$ mixed gas containing 5% $H_2$ before use. The final temperature of reduction was 300° C. The composition of the feed gas was $H_2/CO_2=3$ (volume ratio). The reaction pressure was 3 MPa; the space velocity was 10000 $h^{-1}$; and the evaluation temperature was 300° C. After the reaction was stable for 10 h, sampling analysis was performed. The reaction tail gas was analyzed online by gas chromatography, TCD and FID detectors. The liquid product was collected after sufficient condensation and analyzed by gas chromatography. The test results were shown in Table 1.

TABLE 1

Catalytic Performance of Catalysts in a reaction of $CO_2$ Hydrogenation for Producing Lower Alcohol

| catalyst | main elemental composition of the upper segment of the inner hole* | main elemental composition of the lower segment of the inner hole* | $CO_2$ conversion rate (%) | total alcohol selectivity (%) | alcohol distribution (%) | | |
|---|---|---|---|---|---|---|---|
| | | | | | methanol | $C_{2-5}$OH | isobutanol |
| y1 | 12.12% Zn; 30.3% Al. | 15.48% Cu; 12.38% Zn; 7.74% Al; 7.28% Zr; 1.55% Co. | 30.12 | 29.87 | 60.14 | 29.86 | 15.24 |
| y2 | 14.27% Zn; 28.59% Al. | 11.12% Cu; 11.29% Zn; 9.03% Al; 8.5% Zr; 3.39% Co. | 32.87 | 31.92 | 63.25 | 26.75 | 14.98 |

TABLE 1-continued

Catalytic Performance of Catalysts in a reaction of $CO_2$ Hydrogenation for Producing Lower Alcohol

| catalyst | main elemental composition of the upper segment of the inner hole* | main elemental composition of the lower segment of the inner hole* | $CO_2$ conversion rate (%) | total alcohol selectivity (%) | alcohol distribution (%) | | |
|---|---|---|---|---|---|---|---|
| | | | | | methanol | $C_{2-5}OH$ | isobutanol |
| y3 | 16.22% Zn; 27.03% Al. | 9.3% Cu; 11.15% Zn; 9.3% Al; 7% Zr; 7.44% Co. | 35.14 | 33.81 | 64.15 | 25.85 | 14.98 |
| y4 | 16.23% Zn; 27.02% Al. | 10.08% Cu; 8.06% Zn; 10.08% Al; 9.48% Zr; 5.04% Co. | 34.89 | 36.47 | 60.88 | 29.12 | 20.17 |
| y5 | 12.19% Zn; 29.81% Al. | 11.14% Cu; 7.8% Zn; 7.8% Al; 10.49% Zr; 5.57% Co. | 34.19 | 30.72 | 62.58 | 27.42 | 19.87 |
| y6 | 12.54% Zn; 28.97% Al. | 8.84% Cu; 6.19% Zn; 19.86% Al; 3.82% Zr; 4.42% Co. | 30.87 | 31.42 | 66.12 | 33.88 | 18.97 |
| C1 | — | — | 18.97 | 23.11 | 89.15 | 10.85 | 1.24 |
| U2 | 11.14% Cu; 7.8% Zn; 7.8% Al; 10.49% Zr; 5.57% Co. | 11.14% Cu; 7.8% Zn; 7.8% Al; 10.49% Zr; 5.57% Co. | 20.59 | 25.83 | 79.12 | 20.88 | 5.97 |

*The elemental composition of the active components was determined by the XPS method.

It can be seen from Table 1 that compared with the conventional co-precipitation methods and homogenous supporting methods, the monolithic catalyst prepared by the method of the present invention had higher $CO_2$ conversion rates, total alcohol selectivities and isobutanol selectivities in the reaction of $CO_2$ hydrogenation for producing lower alcohols.

Example 7

A cylindrical cordierite with a cross-sectional diameter of 035 mm, a height of 52.5 mm and an inner hole diameter of 1 mm was immersed in an aqueous solution of aluminum nitrate and urea in an autoclave for treatment (the amount-of-substance ratio of aluminum nitrate to urea was 1.2, and the amount-of-substance concentration of aluminum nitrate was 1 mol/L) at a pressure of 0.5 MPa, at a temperature of 150° C. and for a period of 5 h to obtain a precursor of a coating-containing carrier; the precursor was dried in air at 120° C. for 4 h and calcined at 600° C. for 4 h to obtain a coating-containing carrier.

37.8 g of zinc nitrate and 106.5 g of aluminum nitrate were dissolved in 1400 mL of deionized water to prepare a mixed solution of zinc and aluminum. A suitable amount of nitric acid was added to control the solution to have a pH of 6.0. The upper segment of the above-mentioned coating-containing carrier (½ of the total height) was impregnated in the mixed solution of zinc and aluminum at 30° C. for 8 h. Then, said upper segment was impregnated in a 30° C., 1 mol/L sodium carbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 4 h to obtain a catalyst semi-finished product.

1.88 g of copper nitrate and 18.9 g of zinc nitrate were dissolved in 220 mL of deionized water to prepare a mixed solution of copper and zinc. A suitable amount of nitric acid was added to control the solution to have a pH of 6.0. The lower segment of the above-mentioned coating-containing carrier (½ of the total height) was impregnated in the mixed solution of copper and zinc at 30° C. for 8 h. Then, said lower segment was impregnated in a 30° C., 1 mol/L sodium carbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 4 h to obtain a monolithic catalyst y7.

Example 8

A cylindrical cordierite with a cross-sectional diameter of 135 mm, a height of 63 mm and an inner hole diameter of 2 mm was immersed in an aqueous solution of aluminum nitrate and urea in an autoclave for treatment (the amount-of-substance ratio of aluminum nitrate to urea was 1.8, and the amount-of-substance concentration of aluminum nitrate was 1 mol/L) at a pressure of 1 MPa, at a temperature of 120° C. and for a period of 4 h to obtain a precursor of a coating-containing carrier; the precursor was dried in air at 120° C. for 4 h and calcined at 650° C. for 4 h to obtain a coating-containing carrier.

47.25 g of zinc nitrate and 106.7 g of aluminum nitrate were dissolved in 750 mL of deionized water to prepare a mixed solution of zinc and aluminum. A small amount of nitric acid was added to control the solution to have a pH of 6.5. The upper segment of the above-mentioned coating-containing carrier (9/20 of the total height) was impregnated in the mixed solution of zinc and aluminum at 50° C. for 7 h. Then, said upper segment was impregnated in a 50° C., 1 mol/L sodium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 600° C. for 3 h to obtain a one-time impregnation sample. Then, the aforesaid process of mixed solution impregnation-sodium hydrogencarbonate solution impregnation-washing-drying-calcination was repeated once to obtain a catalyst semi-finished product.

18.8 g of copper nitrate and 94.5 g of zinc nitrate were dissolved in 600 mL of deionized water to prepare a mixed solution of copper and zinc. A small amount of nitric acid was added to control the solution to have a pH of 6.5. The lower segment of the above-mentioned coating-containing carrier (11/20 of the total height) was impregnated in the mixed solution of copper and zinc at 50° C. for 7 h. Then, said lower segment was impregnated in a 50° C., 1 mol/L sodium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 600° C. for 4 h to obtain a one-time impregnation sample. Then, the aforesaid process of mixed solution impregnation-sodium hydrogencarbonate solution impregnation-washing-drying-calcination was repeated once to obtain a monolithic catalyst y8.

Example 9

A cylindrical cordierite with a cross-sectional diameter of 135 mm, a height of 70 mm and an inner hole diameter of 3 mm was immersed in an aqueous solution of aluminum nitrate and urea in an autoclave for treatment (the amount-of-substance ratio of aluminum nitrate to urea was 2, and the amount-of-substance concentration of aluminum nitrate was 1 mol/L) at a pressure of 2 MPa, at a temperature of 100° C. and for a period of 4 h to obtain a precursor of a coating-containing carrier; the precursor of the coating-containing carrier was dried in air at 120° C. for 4 h and calcined at 700° C. for 3 h to obtain the coating-containing carrier.

28.35 g of zinc nitrate and 53.25 g of aluminum nitrate were dissolved in 310 mL of deionized water to prepare a mixed solution of zinc and aluminum having a pH of 7.0. The upper segment of the above-mentioned coating-containing carrier (5/16 of the total height) was impregnated in the mixed solution of zinc and aluminum at 60° C. for 5 h. Then, said upper segment was impregnated in a 60° C., 1 mol/L potassium carbonate solution for 10 min, then washed with water having a conductivity less than 2 S/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 700° C. for 1 h to obtain a one-time impregnation sample. Then, the aforesaid process of mixed solution impregnation-potassium carbonate solution impregnation-washing-drying-calcination was repeated twice to obtain a catalyst semi-finished product.

28.2 g of copper nitrate and 94.5 g of zinc nitrate were dissolved in 650 mL of deionized water to prepare a mixed solution of copper and zinc having a pH of 7.0. The lower segment of the above-mentioned coating-containing carrier (11/16 of the total height) was impregnated in the mixed solution of copper and zinc at 60° C. for 5 h. Then, said lower segment was impregnated in a 60° C., 1 mol/L potassium carbonate solution for 10 min, then washed with water having a conductivity less than 2 S/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 1 h to obtain a one-time impregnation sample. Then, the aforesaid process of mixed solution impregnation-potassium carbonate solution impregnation-washing-drying-calcination was repeated twice to obtain a monolithic catalyst y9.

Example 10

A cylindrical cordierite with a cross-sectional diameter of 135 mm, a height of 105 mm and an inner hole diameter of 3 mm was immersed in an aqueous solution of aluminum nitrate and urea in an autoclave for treatment (the amount-of-substance ratio of aluminum nitrate to urea was 2.5, and the amount-of-substance concentration of aluminum nitrate was 1 mol/L) at a pressure of 3 MPa, at a temperature of 70° C. and for a period of 3 h to obtain a precursor of a coating-containing carrier; the precursor was dried in air at 120° C. for 4 h and calcined at 750° C. for 2 h to obtain a coating-containing carrier.

56.7 g of zinc nitrate and 106.4 g of aluminum nitrate were dissolved in 400 mL of deionized water to prepare a mixed solution of zinc and aluminum. A small amount of nitric acid was added to control the solution to have a pH of 6.5. The upper segment of the above-mentioned coating-containing carrier (2/5 of the total height) was impregnated in the mixed solution of zinc and aluminum at 70° C. for 3 h. Then, said upper segment was impregnated in a 70° C., 1 mol/L potassium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 800° C. for 0.5 h to obtain a one-time impregnation sample. Then, the aforesaid process of mixed solution impregnation-potassium hydrogencarbonate solution impregnation-washing-drying-calcination was repeated twice to obtain a catalyst semi-finished product.

37.6 g of copper nitrate and 94.5 g of zinc nitrate were dissolved in 2500 mL of deionized water to prepare a mixed solution of copper and zinc. A small amount of nitric acid was added to control the solution to have a pH of 6.5. The lower segment of the above-mentioned coating-containing carrier (3/5 of the total height) was impregnated in the mixed solution of copper and zinc at 70° C. for 3 h. Then, said lower segment was impregnated in a 70° C., 1 mol/L potassium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm;

thereafter, it was dried in a drying oven at 90° C. for 4 h, and calcined in air at 500° C. for 2 h to obtain a one-time impregnation sample. Then, the aforesaid process of mixed solution impregnation-potassium hydrogencarbonate solution impregnation-washing-drying-calcination was repeated twice to obtain a monolithic catalyst y10.

Example 11

A cylindrical cordierite with a cross-sectional diameter of 135 mm, a height of 105 mm and an inner hole diameter of 3 mm was immersed in an aqueous solution of aluminum nitrate and urea in an autoclave for treatment (the amount-of-substance ratio of aluminum nitrate to urea was 3, and the amount-of-substance concentration of aluminum nitrate was 1 mol/L) at a pressure of 4 MPa, at a temperature of 100° C. and for a period of 1 h to obtain a precursor of a coating-containing carrier; the precursor was dried in air at 120° C. for 4 h and calcined at 800° C. for 1 h to obtain a coating-containing carrier.

37.8 g of zinc nitrate and 106.5 g of aluminum nitrate were dissolved in 700 mL of deionized water to prepare a mixed solution of zinc and aluminum. A small amount of nitric acid was added to control the solution to have a pH of 6.5. The upper segment of the above-mentioned coating-containing carrier (3/10 of the total height) was impregnated in the mixed solution of zinc and aluminum at 80° C. for 0.5 h. Then, said upper segment was impregnated in a 80° C., 1 mol/L sodium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 800° C. for 0.5 h to obtain a one-time impregnation sample. Then, the aforesaid process of mixed solution impregnation-sodium hydroxide solution impregnation-washing-drying-calcination was repeated twice to obtain a catalyst semi-finished product.

47 g of copper nitrate and 94.5 g of zinc nitrate were dissolved in 50 mL of deionized water to prepare a mixed solution of copper and zinc. A small amount of nitric acid was added to control the solution to have a pH of 6.5. The lower segment of the above-mentioned coating-containing carrier (7/10 of the total height) was impregnated in the mixed solution of copper and zinc at 80° C. for 0.5 h. Then, said lower segment was impregnated in a 80° C., 1 mol/L sodium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 2 h to obtain a one-time impregnation sample. Then, the aforesaid process of mixed solution impregnation-sodium hydroxide solution impregnation-washing-drying-calcination was repeated twice to obtain a monolithic catalyst y11.

Example 12

A cylindrical cordierite with a cross-sectional diameter of Φ35 mm, a height of 210 mm and an inner hole diameter of 5 mm was immersed in an aqueous solution of aluminum nitrate and urea in an autoclave for treatment (the amount-of-substance ratio of aluminum nitrate to urea was 3.5, and the amount-of-substance concentration of aluminum nitrate was 1 mol/L) at a pressure of 6 MPa, at a temperature of 80° C. and for a period of 1 h to obtain a precursor of a coating-containing carrier; the precursor was dried in air at 120° C. for 4 h and calcined at 650° C. for 2 h to obtain a coating-containing carrier.

37.8 g of zinc nitrate and 106.5 g of aluminum nitrate were dissolved in 700 mL of deionized water to prepare a mixed solution of zinc and aluminum. A small amount of nitric acid was added to control the solution to have a pH of 6.5. The upper segment of the above-mentioned coating-containing carrier (1/4 of the total height) was impregnated in the mixed solution of zinc and aluminum at 50° C. for 1 h. Then, said upper segment was impregnated in a 50° C., 1 mol/L potassium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 800° C. for 0.5 h to obtain a one-time impregnation sample. Then, the aforesaid process of mixed solution impregnation-potassium hydroxide solution impregnation-washing-drying-calcination was repeated twice to obtain a catalyst semi-finished product.

47 g of copper nitrate and 94.5 g of zinc nitrate were dissolved in 1500 mL of deionized water to prepare a mixed solution of copper and zinc. A small amount of nitric acid was added to control the solution to have a pH of 6.5. The lower segment of the above-mentioned coating-containing carrier (3/4 of the total height) was impregnated in the mixed solution of copper and zinc at 50° C. for 0.5 h. Then, said lower segment was impregnated in a 50° C., 1 mol/L potassium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 1 h to obtain a one-time impregnation sample. Then, the aforesaid process of mixed solution impregnation-potassium hydroxide solution impregnation-washing-drying-calcination was repeated twice to obtain a monolithic catalyst y12.

Comparative Example 3

188 g of copper nitrate, 113.4 g of zinc nitrate and 42.6 g of aluminum nitrate were dissolved in 1200 mL of deionized water to obtain a mixed nitrate solution, and the solution was preheated to 65° C.; 1 mol/L sodium carbonate aqueous solution was formulated and preheated to 65° C.; the mixed nitrate solution and sodium carbonate solution were concurrently added to 300 mL of 50° C. deionized water with pH maintained at 7.2, and then aged in situ for 1 h; a filtration was carried out, and the deionized water having a conductivity less than 2 μS/cm was used for suction filtration and washing of filter cake, until the conductivity of filter liquor was less than 5 μS/cm; ethanol was then used for suction filtration and washing, till the water content in the filter cake was less than 100 ppm, thereby obtaining a catalyst precursor; the precursor was dried in a drying oven at 90° C. for 4 h, and calcined in air at 350° C. for 2 h; the resulting powder was tableted and shaped into a cylinder (Φ5 mm×5 mm) to obtain a catalyst C3.

Comparative Example 4

A cylindrical cordierite with a cross-sectional diameter of Φ35 mm, a height of 210 mm and an inner hole diameter of 5 mm was immersed in an aqueous solution of aluminum nitrate and urea in an autoclave for treatment (the amount-of-substance ratio of aluminum nitrate to urea was 3.5 and the amount-of-substance concentration of aluminum nitrate was 1 mol/L) at a pressure of 6 MPa, at a temperature of 80° C. and for a period of 1 h to obtain a precursor of a coating-containing carrier; the precursor was dried in air at 120° C. for 4 h and calcined at 650° C. for 2 h to obtain a coating-containing carrier.

determined to result in an initial catalytic performance; then, the feed gas was supplemented by 5% water vapor, and then after stabilization for 10 h, the sample was determined to result in a catalytic performance after hydrothermal resistance. The products were analyzed by gas chromatography. The evaluation results were shown in Table 1, wherein hydrothermal stability=(initial methanol space-time yield–methanol space-time yield after hydrothermal resistance)/initial methanol space-time yield×100%.

TABLE 2

Catalytic Performance of Catalysts in a reaction of $CO_2$ Hydrogenation for Producing Methanol

| catalyst | main elemental composition of the upper segment of the inner hole* | main elemental composition of the lower segment of the inner hole* | initial catalytic performance | | catalytic performance after heat resistance | | hydrothermal stability/% |
|---|---|---|---|---|---|---|---|
| | | | $CO_2$ conversion rate/% | methanol space-time yield/ (g/h/mL) | $CO_2$ conversion rate/% | methanol space-time yield/ (g/h/mL) | |
| y7 | 12.15% Zn; 30% Al. | 4.55% Cu; 45.45% Zn. | 45.48 | 1.62 | 40.48 | 1.45 | 89 |
| y8 | 14.27% Zn; 28.59% Al. | 9.09% Cu; 41.67% Zn. | 46.48 | 1.66 | 39.51 | 1.41 | 85 |
| y9 | 16.22% Zn; 27.03% Al. | 11.54% Cu; 38.46% Zn. | 47.48 | 1.70 | 39.41 | 1.41 | 83 |
| y10 | 16.23% Zn; 27.02% Al. | 16.67% Cu; 35.71% Zn. | 49.00 | 1.75 | 42.14 | 1.51 | 86 |
| y11 | 12.12% Zn; 30.3% Al. | 16.67% Cu; 33.33% Zn. | 51.00 | 1.82 | 45.90 | 1.64 | 90 |
| y12 | 12.17% Zn; 30.5% Al. | 20% Cu; 33.5% Zn. | 52.00 | 1.86 | 45.24 | 1.62 | 87 |
| C3 | — | — | 22.0 | 0.63 | 14.74 | 0.42 | 67 |
| U4 | 7.94% Cu; 22.22% Zn; 15.87% Al. | 7.94% Cu; 22.22% Zn; 15.87% Al. | 20.0 | 0.57 | 15.20 | 0.43 | 76 |

*The elemental composition of the active components was determined by the XPS method.

47 g of copper nitrate, 132.3 g of zinc nitrate and 106.5 g of aluminum nitrate were dissolved in 2000 mL of deionized water to prepare a mixed solution of copper, zinc and aluminum. A small amount of nitric acid was added to control the solution to have a pH of 6.5. The above-mentioned coating-containing carrier was firstly impregnated in the mixed solution of copper, zinc and aluminum at 50° C. for 1 h. Then, said coating-containing carrier was impregnated in a 50° C., 1 mol/L potassium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 1 h to obtain a one-time impregnation sample. Then, the aforesaid process of mixed solution impregnation-potassium hydroxide solution impregnation-washing-drying-calcination was repeated twice to obtain a monolithic catalyst U4.

Activity test conditions: the activities of the catalysts were evaluated on a fixed bed isothermal reactor, and the reaction tube had an inner diameter of 35 mm and a length of 1200 mm. The catalysts were subjected to in situ reduction in a reactor with a $H_2/N_2$ mixed gas containing 5% $H_2$ before use, and the final temperature of the reduction was 300° C. The composition of the feed gas was $H_2/CO_2$=3 (volume ratio). The reaction pressure was 5 MPa; the space velocity was 10000 $h^{-1}$; and the evaluation temperature was 300° C. After the reaction was stable for 10 h, the sample was It can be seen from Table 2 that compared with the conventional co-precipitation methods and homogenous supporting methods, the monolithic catalysts prepared by the method of the present invention had higher $CO_2$ conversion rates and methanol space-time yields in the reaction of $CO_2$ hydrogenation for producing methanol. At the same time, the hydrothermal stability of the catalysts was also improved significantly.

Example 13

A cylindrical cordierite with a cross-sectional diameter of 035 mm, a height of 52.5 mm and an inner hole diameter of 1 mm was immersed in an aqueous solution of aluminum nitrate and urea in an autoclave for treatment (the amount-of-substance ratio of aluminum nitrate to urea was 1.2, and the amount-of-substance concentration of aluminum nitrate was 1 mol/L) at a pressure of 0.5 MPa, at a temperature of 150° C. and for a period of 5 h to obtain a precursor of a coating-containing carrier; the precursor was dried in air at 120° C. for 4 h and calcined at 600° C. for 4 h to obtain a coating-containing carrier.

37.8 g of zinc nitrate and 106.5 g of aluminum nitrate were dissolved in 1400 mL of deionized water to prepare a mixed solution of zinc and aluminum. A suitable amount of nitric acid was added to control the solution to have a pH of 6.0. The upper segment of the above-mentioned coating-containing carrier (½ of the total height) was impregnated in the mixed solution of zinc and aluminum at 30° C. for 8 h. Then, said upper segment was impregnated in a 30° C., 1 mol/L sodium carbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 4 h to obtain a catalyst semi-finished product.

1.83 g of nickel nitrate and 21.3 g of aluminum nitrate were dissolved in 220 mL of deionized water to prepare a mixed solution of nickel and aluminum. A suitable amount of nitric acid was added to control the solution to have a pH of 6.0. The lower segment of the above-mentioned coating-containing carrier (½ of the total height) was impregnated in the mixed solution of nickel and aluminum at 30° C. for 8 h. Then, said lower segment was impregnated in a 30° C., 1 mol/L sodium carbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 4 h to obtain a monolithic catalyst y13.

Example 14

A cylindrical cordierite with a cross-sectional diameter of Φ35 mm, a height of 63 mm and an inner hole diameter of 2 mm was immersed in an aqueous solution of aluminum nitrate and urea in an autoclave for treatment (the amount-of-substance ratio of aluminum nitrate to urea was 1.8, and the amount-of-substance concentration of aluminum nitrate was 1 mol/L) at a pressure of 1 MPa, at a temperature of 120° C. and for a period of 4 h to obtain a precursor of a coating-containing carrier; the precursor was dried in air at 120° C. for 4 h and calcined at 650° C. for 4 h to obtain a coating-containing carrier.

47.25 g of zinc nitrate and 106.7 g of aluminum nitrate were dissolved in 750 mL of deionized water to prepare a mixed solution of zinc and aluminum. A small amount of nitric acid was added to control the solution to have a pH of 6.5. The upper segment of the above-mentioned coating-containing carrier (7/16 of the total height) was impregnated in the mixed solution of zinc and aluminum at 50° C. for 7 h. Then, said upper segment was impregnated in a 50° C., 1 mol/L sodium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 600° C. for 3 h to obtain a one-time impregnation sample. Then, the aforesaid process of mixed solution impregnation-sodium hydrogencarbonate solution impregnation-washing-drying-calcination was repeated once to obtain a catalyst semi-finished product.

18.27 g of nickel nitrate and 106.5 g of aluminum nitrate were dissolved in 1200 mL of deionized water to prepare a mixed solution of nickel and aluminum. A small amount of nitric acid was added to control the solution to have a pH of 6.5. The lower segment of the above-mentioned coating-containing carrier (9/16 of the total height) was impregnated in the mixed solution of nickel and aluminum at 50° C. for 7 h. Then, said lower segment was impregnated in a 50° C., 1 mol/L sodium hydrogencarbonate solution for 10 min, then washed with water having a conductivity less than 2 S/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 600° C. for 4 h to obtain a one-time impregnation sample. Then, the aforesaid process of mixed solution impregnation-sodium hydrogencarbonate solution impregnation-washing-drying-calcination was repeated once to obtain a monolithic catalyst y14.

Example 15

A cylindrical cordierite with a cross-sectional diameter of 135 mm, a height of 70 mm and an inner hole diameter of 3 mm was immersed in an aqueous solution of aluminum nitrate and urea in an autoclave for treatment (the amount-of-substance ratio of aluminum nitrate to urea was 2, and the amount-of-substance concentration of aluminum nitrate was 1 mol/L) at a pressure of 2 MPa, at a temperature of 100° C. and for a period of 4 h to obtain a precursor of a coating-containing carrier; the precursor was dried in air at 120° C. for 4 h and calcined at 700° C. for 3 h to obtain a coating-containing carrier.

28.35 g of zinc nitrate and 53.25 g of aluminum nitrate were dissolved in 310 mL of deionized water to prepare a mixed solution of zinc and aluminum. The solution had a pH of 7.0. The upper segment of the above-mentioned coating-containing carrier (⅖ of the total height) was impregnated in the mixed solution of zinc and aluminum at 60° C. for 5 h. Then, said upper segment was impregnated in a 60° C., 1 mol/L potassium carbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 700° C. for 1 h to obtain a one-time impregnation sample. Then, the aforesaid process of mixed solution impregnation-potassium carbonate solution impregnation-washing-drying-calcination was repeated twice to obtain a catalyst semi-finished product.

27.4 g of nickel nitrate and 106.5 g of aluminum nitrate were dissolved in 650 mL of deionized water to prepare a mixed solution of nickel and aluminum. The solution had a pH of 7.0. The lower segment of the above-mentioned coating-containing carrier (⅗ of the total height) was impregnated in the mixed solution of nickel and aluminum at 60° C. for 5 h. Then, said lower segment was impregnated in a 60° C., 1 mol/L potassium carbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 1 h to obtain a one-time impregnation sample. Then, the aforesaid process of mixed solution impregnation-potassium carbonate solution impregnation-washing-drying-calcination was repeated twice to obtain a monolithic catalyst y15.

Example 16

A cylindrical cordierite with a cross-sectional diameter of Φ35 mm, a height of 105 mm and an inner hole diameter of 3 mm was immersed in an aqueous solution of aluminum nitrate and urea in an autoclave for treatment (the amount-of-substance ratio of aluminum nitrate to urea was 2.5, and the amount-of-substance concentration of aluminum nitrate was 1 mol/L) at a pressure of 3 MPa, at a temperature of 70° C. and for a period of 3 h to obtain a precursor of a coating-containing carrier; the precursor was dried in air at 120° C. for 4 h and calcined at 750° C. for 2 h to obtain a coating-containing carrier.

56.7 g of zinc nitrate and 106.4 g of aluminum nitrate were dissolved in 400 mL of deionized water to prepare a mixed solution of zinc and aluminum. A small amount of nitric acid was added to control the solution to have a pH of 6.5. The upper segment of the above-mentioned coating-containing carrier (5/16 of the total height) was impregnated in the mixed solution of zinc and aluminum at 70° C. for 3 h. Then, said upper segment was impregnated in a 70° C., 1 mol/L potassium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 800° C. for 0.5 h to obtain a one-time impregnation sample. Then, the aforesaid process of mixed solution impregnation-potassium hydrogencarbonate solution impregnation-washing-drying-calcination was repeated twice to obtain a catalyst semi-finished product.

36.54 g of nickel nitrate and 106.5 g of aluminum nitrate were dissolved in 2500 mL of deionized water to prepare a mixed solution of nickel and aluminum. A small amount of nitric acid was added to control the solution to have a pH of 6.5. The lower segment of the above-mentioned coating-containing carrier (11/16 of the total height) was impregnated in the mixed solution of nickel and aluminum at 70° C. for 3 h. Then, said lower segment was impregnated in a 70° C., 1 mol/L potassium hydrogencarbonate solution for 10 min, then washed with water having a conductivity less than 2 S/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 2 h to obtain a one-time impregnation sample. Then, the aforesaid process of mixed solution impregnation-potassium hydrogencarbonate solution impregnation-washing-drying-calcination was repeated twice to obtain a monolithic catalyst y16.

Example 17

A cylindrical cordierite with a cross-sectional diameter of 035 mm, a height of 105 mm and an inner hole diameter of 3 mm was immersed in an aqueous solution of aluminum nitrate and urea in an autoclave for treatment (the amount-of-substance ratio of aluminum nitrate to urea was 3, and the amount-of-substance concentration of aluminum nitrate was 1 mol/L) at a pressure of 4 MPa, at a temperature of 100° C. and for a period of 1 h to obtain a precursor of a coating-containing carrier; the precursor was dried in air at 120° C. for 4 h and calcined at 800° C. for 1 h to obtain a coating-containing carrier.

37.8 g of zinc nitrate and 106.5 g of aluminum nitrate were dissolved in 700 mL of deionized water to prepare a mixed solution of zinc and aluminum. A small amount of nitric acid was added to control the solution to have a pH of 6.5. The upper segment of the above-mentioned coating-containing carrier (3/10 of the total height) was impregnated in the mixed solution of zinc and aluminum at 80° C. for 0.5 h. Then, said upper segment was impregnated in a 80° C., 1 mol/L sodium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 800° C. for 0.5 h to obtain a one-time impregnation sample. Then, the aforesaid process of mixed solution impregnation-sodium hydroxide solution impregnation-washing-drying-calcination was repeated twice to obtain a catalyst semi-finished product.

45.68 g of nickel nitrate and 106.5 g of aluminum nitrate were dissolved in 50 mL of deionized water to prepare a mixed solution of nickel and aluminum. A small amount of nitric acid was added to control the solution to have a pH of 6.5. The lower segment of the above-mentioned coating-containing carrier (7/10 of the total height) was impregnated in the mixed solution of nickel and aluminum at 80° C. for 0.5 h. Then, said lower segment was impregnated in a 80° C., 1 mol/L sodium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 2 h to obtain a one-time impregnation sample. Then, the aforesaid process of mixed solution impregnation-sodium hydroxide solution impregnation-washing-drying-calcination was repeated twice to obtain a monolithic catalyst y17.

Example 18

A cylindrical cordierite with a cross-sectional diameter of Φ35 mm, a height of 210 mm and an inner hole diameter of 5 mm was immersed in an aqueous solution of aluminum nitrate and urea in an autoclave for treatment (the amount-of-substance ratio of aluminum nitrate to urea was 3.5, and the amount-of-substance concentration of aluminum nitrate was 1 mol/L) at a pressure of 6 MPa, at a temperature of 80° C. and for a period of 1 h to obtain a precursor of a coating-containing carrier; the precursor was dried in air at 120° C. for 4 h and calcined at 650° C. for 2 h to obtain a coating-containing carrier.

37.8 g of zinc nitrate and 106.5 g of aluminum nitrate were dissolved in 700 mL of deionized water to prepare a mixed solution of zinc and aluminum. A small amount of nitric acid was added to control the solution to have a pH of 6.5. The upper segment of the above-mentioned coating-containing carrier (¼ of the total height) was impregnated in the mixed solution of zinc and aluminum at 50° C. for 1 h. Then, said upper segment was impregnated in a 50° C., 1 mol/L potassium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 800° C. for 0.5 h to obtain a one-time impregnation sample. Then, the aforesaid process of mixed solution impregnation-potassium hydroxide solution impregnation-washing-drying-calcination was repeated twice to obtain a catalyst semi-finished product.

45.68 g of nickel nitrate and 106.5 g of aluminum nitrate were dissolved in 1500 mL of deionized water to prepare a mixed solution of nickel and aluminum. A small amount of nitric acid was added to control the solution to have a pH of 6.5. The lower segment of the above-mentioned coating-containing carrier (¾ of the total height) was impregnated in the mixed solution of copper, nickel and aluminum at 50° C. for 0.5 h. Then, said lower segment was impregnated in a 50° C., 1 mol/L potassium hydroxide solution for 10 min, then washed with water having a conductivity less than 2 µS/cm, until the conductivity of the washing liquid was less than 5 µS/cm; then it was washed with anhydrous ethanol, till the water content in the washing liquid was less than 100 ppm; thereafter, it was dried in a drying oven at 90° C. for 4 h, and calcined in air at 500° C. for 1 h to obtain a one-time impregnation sample. Then, the aforesaid process of mixed solution impregnation-potassium hydroxide solution impregnation-washing-drying-calcination was repeated twice to obtain a monolithic catalyst y18.

Comparative Example 5

45.68 g of nickel nitrate and 106.5 g of aluminum nitrate were dissolved in 1000 mL of deionized water to obtain a mixed nitrate solution, and the solution was preheated to 65° C.; 1 mol/L sodium carbonate aqueous solution was formulated and preheated to 65° C.; the mixed nitrate solution and sodium carbonate solution were concurrently added to 300 mL of 50° C. deionized water with pH maintained at 7.2, and then aged in situ for 30 min; a filtration was carried out, and the deionized water having a conductivity less than 2 µS/cm was used for suction filtration and washing of filter cake, until the conductivity of filter liquor was less than 5 µS/cm; ethanol was then used for suction filtration and washing, till the water content in the filter cake was less than 100 ppm, thereby obtaining a catalyst precursor; the precursor was dried in a drying oven at 90° C. for 4 h, and calcined in air at 500° C. for 2 h; 3% graphite and water were added to the resulting powder for tableting and shaping into a cylinder (Φ5 mm×5 mm) to obtain a catalyst C5.

Comparative Example 6

A cylindrical cordierite with a cross-sectional diameter of Φ35 mm, a height of 210 mm and an inner hole diameter of 5 mm was immersed in an aqueous solution of aluminum nitrate and urea in an autoclave for treatment (the amount-of-substance ratio of aluminum nitrate to urea was 3.5, and the amount-of-substance concentration of aluminum nitrate was 1 mol/L) at a pressure of 6 MPa, at a temperature of 80° C. and for a period of 1 h to obtain a precursor of a coating-containing carrier; the precursor was dried in air at 120° C. for 4 h and calcined at 650° C. for 2 h to obtain a coating-containing carrier.

45.68 g of nickel nitrate and 106.5 g of aluminum nitrate were dissolved in 2000 mL of deionized water to prepare a mixed solution of nickel and aluminum. A small amount of nitric acid was added to control the solution to have a pH of 6.5. The above-mentioned coating-containing carrier was firstly impregnated in the mixed solution of nickel and aluminum at 50° C. for 1 h. Then, said coating-containing carrier was impregnated in a 50° C., 1 mol/L potassium hydroxide solution for 10 min, then washed with water having a conductivity less than 2 µS/cm, until the conductivity of the washing liquid was less than 5 µS/cm; then it was washed with anhydrous ethanol, till the water content in the washing liquid was less than 100 ppm; thereafter, it was dried in a drying oven at 90° C. for 4 h, and calcined in air at 500° C. for 1 h to obtain a one-time impregnation sample. Then, the aforesaid process of mixed solution impregnation-potassium hydroxide solution impregnation-washing-drying-calcination was repeated twice to obtain a monolithic catalyst U6.

Activity test conditions: the activity of the catalyst was evaluated on a fixed bed isothermal reactor, and the reaction tube had an inner diameter of 35 mm and a length of 1200 mm. The C catalyst (cylindrical, Φ5×5 mm) was charged in an amount of 200 mL. The catalyst was subjected to a normal pressure in situ reduction in a reactor with $H_2$ before use, and the space velocity was 1500 $h^{-1}$, the temperature was 400° C., and the reduction was carried out for 3 h. The composition of the feed gas was $H_2/CO_2=4$ (volume ratio). The reaction pressure was 1.5 MPa; the space velocity was 15000 $h^{-1}$; and the evaluation temperature was 600° C. The product was analyzed by gas chromatography (Agilent 7820A, thermal conductivity cell detector, TDX-01 carbon molecular sieve chromatographic column, carrier gas $H_2$, mainly analyzing CO, $CO_2$ and $CH_4$ in the gas). The evaluation results were shown in Table 1, wherein $CO_2$ conversion rate (%)=(CO+$CH_4$)/(CO+$CO_2$+$CH_4$).

TABLE 3

Catalytic Performance of Catalysts in a reaction of $CO_2$ Hydrogenation for Producing Methane

| catalyst | main elemental composition of the upper segment of the inner hole[1] | main elemental composition of the lower segment of the inner hole[1] | dry basis composition of outlet gas (%) | | | | $CO_2$ conversion rate (%) | carbon content of catalyst surface area after 1000 h of reaction (wt %) [2] |
|---|---|---|---|---|---|---|---|---|
| | | | $CO_2$ | CO | $CH_4$ | $H_2$ | | |
| y13 | 12.12% Zn; 30.3% Al. | 3.71% Ni; 37.03% Al. | 3.19 | 6.46 | 58.21 | 32.14 | 95.3 | 0 |
| y14 | 14.27% Zn; 32.22% Al. | 6.9% Ni; 34.48% Al. | 2.32 | 6.80 | 61.21 | 29.67 | 96.7 | 0 |
| y15 | 16.22% Zn; 27.03% Al. | 9.68% Ni; 32.26% Al. | 1.11 | 7.26 | 65.4 | 26.23 | 98.5 | 0 |
| y16 | 16.23% Zn; 30.45% Al. | 12.12% Ni; 32.26% Al. | 2.82 | 6.61 | 59.45 | 31.12 | 95.9 | 0 |
| y17 | 12.12% Zn; 30.4% Al. | 14.29% Ni; 28.57% Al. | 1.59 | 7.08 | 63.72 | 27.61 | 97.8 | 0 |
| y18 | 12.12% Zn; 34.15% Al. | 14.29% Ni; 28.56% Al. | 0.82 | 7.38 | 66.39 | 25.41 | 98.9 | 0 |

TABLE 3-continued

Catalytic Performance of Catalysts in a reaction of $CO_2$ Hydrogenation for Producing Methane

| catalyst | main elemental composition of the upper segment of the inner hole*[1] | main elemental composition of the lower segment of the inner hole*[1] | dry basis composition of outlet gas (%) | | | | $CO_2$ conversion rate (%) | carbon content of catalyst surface area after 1000 h of reaction (wt %) *[2] |
|---|---|---|---|---|---|---|---|---|
| | | | $CO_2$ | CO | $CH_4$ | $H_2$ | | |
| C5 | — | — | 10.02 | 6.24 | 24.96 | 58.78 | 75.7 | 0.8 |
| U6 | 14.28% Zn; 28.57% Al. | 14.28% Zn; 28.57% Al. | 9.31 | 6.68 | 26.72 | 57.29 | 78.2 | 0.3 |

*[1]The elemental composition of the active components was determined by the XPS method.
*[2] Data were obtained by X-ray fluorescence spectrometry.

It can be seen from Table 3 that in the reaction of $CO_2$ hydrogenation for producing methane, the catalyst prepared by the technology of the present invention has the higher $CO_2$ conversion rates and the methane content in the product gas, compared with the conventional co-precipitated and monolithic homogeneously supported catalysts. There was no carbon deposition in the methanation reaction for a continuous period of 1000 h.

Example 19

A cylindrical cordierite with a cross-sectional diameter of 135 mm, a height of 52.5 mm and an inner hole diameter of 1 mm was immersed in an aqueous solution of aluminum nitrate and urea in an autoclave for treatment (the amount-of-substance ratio of aluminum nitrate to urea was 1.2, and the amount-of-substance concentration of aluminum nitrate was 1 mol/L) at a pressure of 0.5 MPa, at a temperature of 150° C. and for a period of 5 h to obtain a precursor of a coating-containing carrier; the precursor was dried in air at 120° C. for 4 h and calcined at 600° C. for 4 h to obtain a coating-containing carrier.

31.33 g of copper nitrate, 9.45 g of zinc nitrate and 17.75 g of aluminum nitrate were dissolved in 600 mL of deionized water to prepare a mixed solution of copper, zinc and aluminum. A suitable amount of nitric acid was added to control the solution to have a pH of 6.0. The upper segment of the above-mentioned coating-containing carrier (⅕ of the total height) was impregnated in the mixed solution of copper, zinc and aluminum at 30° C. for 8 h. Then, said upper segment was impregnated in a 30° C., 1 mol/L sodium carbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 300° C. for 4 h to obtain a catalyst semi-finished product.

31.33 g of copper nitrate, 9.45 g of zinc nitrate and 53.16 g of zirconium nitrate were dissolved in 770 mL of deionized water to prepare a mixed solution of copper, zinc and zirconium. A suitable amount of nitric acid was added to control the solution to have a pH of 6.0. The lower segment of the above-mentioned coating-containing carrier (⅘ of the total height) was impregnated in the mixed solution of copper, zinc and zirconium at 30° C. for 8 h. Then, said lower segment was impregnated in a 30° C., 1 mol/L sodium carbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 300° C. for 4 h to obtain a monolithic catalyst y19.

Example 20

A cylindrical cordierite with a cross-sectional diameter of 035 mm, a height of 63 mm and an inner hole diameter of 2 mm was immersed in an aqueous solution of aluminum nitrate and urea in an autoclave for treatment (the amount-of-substance ratio of aluminum nitrate to urea was 1.8, and the amount-of-substance concentration of aluminum nitrate was 1 mol/L) at a pressure of 1 MPa, at a temperature of 120° C. and for a period of 4 h to obtain a precursor of a coating-containing carrier; the precursor was dried in air at 120° C. for 4 h and calcined at 650° C. for 4 h to obtain a coating-containing carrier.

31.33 g of copper nitrate, 15.75 g of zinc nitrate and 14.2 g of aluminum nitrate were dissolved in 320 mL of deionized water to prepare a mixed solution of copper, zinc and aluminum. A small amount of nitric acid was added to control the solution to have a pH of 6.5. The upper segment of the above-mentioned coating-containing carrier (⅓ of the total height) was impregnated in the mixed solution of copper, zinc and aluminum at 50° C. for 7 h. Then, said upper segment was impregnated in a 50° C., 1 mol/L sodium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 400° C. for 3.5 h to obtain a one-time impregnation sample. Then, the aforesaid process of mixed solution impregnation-sodium hydrogencarbonate solution impregnation-washing-drying-calcination was repeated once to obtain a catalyst semi-finished product.

31.33 g of copper nitrate, 15.75 g of zinc nitrate and 28.4 g of zirconium nitrate were dissolved in 380 mL of deionized water to prepare a mixed solution of copper, zinc and zirconium. A small amount of nitric acid was added to control the solution to have a pH of 6.5. The lower segment of the above-mentioned coating-containing carrier (⅔ of the total height) was impregnated in the mixed solution of copper, zinc and zirconium at 50° C. for 7 h. Then, said lower segment was impregnated in a 50° C., 1 mol/L sodium hydrogencarbonate solution for 10 min, then washed with water having a conductivity less than 2 μS/cm, until the conductivity of the washing liquid was less than 5 μS/cm;

then it was washed with anhydrous ethanol, till the water content in the washing liquid was less than 100 ppm; thereafter, it was dried in a drying oven at 90° C. for 4 h, and calcined in air at 400° C. for 4 h to obtain a one-time impregnation sample. Then, the aforesaid process of mixed solution impregnation-sodium hydrogencarbonate solution impregnation-washing-drying-calcination was repeated once to obtain a monolithic catalyst y20.

Example 21

A cylindrical cordierite with a cross-sectional diameter of 035 mm, a height of 70 mm and an inner hole diameter of 3 mm was immersed in an aqueous solution of aluminum nitrate and urea in an autoclave for treatment (the amount-of-substance ratio of aluminum nitrate to urea was 2, and the amount-of-substance concentration of aluminum nitrate was 1 mol/L) at a pressure of 2 MPa, at a temperature of 100° C. and for a period of 4 h to obtain a precursor of a coating-containing carrier; the precursor was dried in air at 120° C. for 4 h and calcined at 700° C. for 3 h to obtain a coating-containing carrier.

31.33 g of copper nitrate, 25.2 g of zinc nitrate and 10.65 g of aluminum nitrate were dissolved in 175 mL of deionized water to prepare a mixed solution of copper, zinc and aluminum. The solution had a pH of 7.0. The upper segment of the above-mentioned coating-containing carrier (3/7 of the total height) was impregnated in the mixed solution of copper, zinc and aluminum at 60° C. for 5 h. Then, said upper segment was impregnated in a 60° C., 1 mol/L potassium carbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 450° C. for 3 h to obtain a one-time impregnation sample. Then, the aforesaid process of mixed solution impregnation-potassium carbonate solution impregnation-washing-drying-calcination was repeated twice to obtain a catalyst semi-finished product.

31.33 g of copper nitrate, 25.2 g of zinc nitrate and 26.58 g of zirconium nitrate were dissolved in 190 mL of deionized water to prepare a mixed solution of copper, zinc and zirconium. The solution had a pH of 7.0. The lower segment of the above-mentioned coating-containing carrier (4/7 of the total height) was impregnated in the mixed solution of copper, zinc and zirconium at 60° C. for 5 h. Then, said lower segment was impregnated in a 60° C., 1 mol/L potassium carbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 450° C. for 3 h to obtain a one-time impregnation sample. Then, the aforesaid process of mixed solution impregnation-potassium carbonate solution impregnation-washing-drying-calcination was repeated twice to obtain a monolithic catalyst y21.

Example 22

A cylindrical cordierite with a cross-sectional diameter of 035 mm, a height of 105 mm and an inner hole diameter of 3 mm was immersed in an aqueous solution of aluminum nitrate and urea in an autoclave for treatment (the amount-of-substance ratio of aluminum nitrate to urea was 2.5, and the amount-of-substance concentration of aluminum nitrate was 1 mol/L) at a pressure of 3 MPa, at a temperature of 70° C. and for a period of 3 h to obtain a precursor of a coating-containing carrier; the precursor was dried in air at 120° C. for 4 h and calcined at 750° C. for 2 h to obtain a coating-containing carrier.

31.33 g of copper nitrate, 31.5 g of zinc nitrate and 7.1 g of aluminum nitrate were dissolved in 370 mL of deionized water to prepare a mixed solution of copper, zinc and aluminum. A small amount of nitric acid was added to control the solution to have a pH of 6.5. The upper segment of the above-mentioned coating-containing carrier (½ of the total height) was impregnated in the mixed solution of copper, zinc and aluminum at 70° C. for 3 h. Then, said upper segment was impregnated in a 70° C., 1 mol/L potassium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 0.5 h to obtain a one-time impregnation sample. Then, the aforesaid process of mixed solution impregnation-potassium hydrogencarbonate solution impregnation-washing-drying-calcination was repeated twice to obtain a catalyst semi-finished product.

31.33 g of copper nitrate, 31.5 g of zinc nitrate and 21.27 g of zirconium nitrate were dissolved in 400 mL of deionized water to prepare a mixed solution of copper, zinc and zirconium. A small amount of nitric acid was added to control the solution to have a pH of 6.5. The lower segment of the above-mentioned coating-containing carrier (½ of the total height) was impregnated in the mixed solution of copper, zinc and zirconium at 70° C. for 3 h. Then, said lower segment was impregnated in a 70° C., 1 mol/L potassium hydrogencarbonate solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 500° C. for 0.5 h to obtain a one-time impregnation sample. Then, the aforesaid process of mixed solution impregnation-potassium hydrogencarbonate solution impregnation-washing-drying-calcination was repeated twice to obtain a monolithic catalyst y22.

Example 23

A cylindrical cordierite with a cross-sectional diameter of 035 mm, a height of 105 mm and an inner hole diameter of 3 mm was immersed in an aqueous solution of aluminum nitrate and urea in an autoclave for treatment (the amount-of-substance ratio of aluminum nitrate to urea was 3, and the amount-of-substance concentration of aluminum nitrate was 1 mol/L) at a pressure of 4 MPa, at a temperature of 100° C. and for a period of 1 h to obtain a precursor of a coating-containing carrier; the precursor was dried in air at 120° C. for 4 h and calcined at 800° C. for 1 h to obtain a coating-containing carrier.

31.33 g of copper nitrate, 37.8 g of zinc nitrate and 3.55 g of aluminum nitrate were dissolved in 380 mL of deionized water to prepare a mixed solution of copper, zinc and aluminum. A small amount of nitric acid was added to control the solution to have a pH of 6.5. The upper segment of the above-mentioned coating-containing carrier (⅔ of the total height) was impregnated in the mixed solution of copper, zinc and aluminum at 80° C. for 0.5 h. Then, said upper segment was impregnated in a 80° C., 1 mol/L sodium hydroxide solution for 10 min, then washed with water having a conductivity less than 2 µS/cm, until the conductivity of the washing liquid was less than 5 µS/cm; then it was washed with anhydrous ethanol, till the water content in the washing liquid was less than 100 ppm; thereafter, it was dried in a drying oven at 90° C. for 4 h, and calcined in air at 400° C. for 1 h to obtain a one-time impregnation sample. Then, the aforesaid process of mixed solution impregnation-sodium hydroxide solution impregnation-washing-drying-calcination was repeated twice to obtain a catalyst semi-finished product.

31.33 g of copper nitrate, 37.8 g of zinc nitrate and 10.64 g of zirconium nitrate were dissolved in 400 mL of deionized water to prepare a mixed solution of copper, zinc and zirconium. A small amount of nitric acid was added to control the solution to have a pH of 6.5. The lower segment of the above-mentioned coating-containing carrier (⅓ of the total height) was impregnated in the mixed solution of copper, zinc and zirconium at 80° C. for 0.5 h. Then, said lower segment was impregnated in a 80° C., 1 mol/L sodium hydroxide solution for 10 min, then washed with water having a conductivity less than 2 µS/cm, until the conductivity of the washing liquid was less than 5 µS/cm; then it was washed with anhydrous ethanol, till the water content in the washing liquid was less than 100 ppm; thereafter, it was dried in a drying oven at 90° C. for 4 h, and calcined in air at 400° C. for 1 h to obtain a one-time impregnation sample. Then, the aforesaid process of mixed solution impregnation-sodium hydroxide solution impregnation-washing-drying-calcination was repeated twice to obtain a monolithic catalyst y23.

Example 24

A cylindrical cordierite with a cross-sectional diameter of Φ35 mm, a height of 210 mm and an inner hole diameter of 5 mm was immersed in an aqueous solution of aluminum nitrate and urea in an autoclave for treatment (the amount-of-substance ratio of aluminum nitrate to urea was 3.5, and the amount-of-substance concentration of aluminum nitrate was 1 mol/L) at a pressure of 6 MPa, at a temperature of 80° C. and for a period of 1 h to obtain a precursor of a coating-containing carrier; the precursor was dried in air at 120° C. for 4 h and calcined at 650° C. for 2 h to obtain a coating-containing carrier.

31.33 g of copper nitrate, 15.75 g of zinc nitrate and 10.65 g of aluminum nitrate were dissolved in 300 mL of deionized water to prepare a mixed solution of copper, zinc and aluminum. A small amount of nitric acid was added to control the solution to have a pH of 6.5. The upper segment of the above-mentioned coating-containing carrier (¾ of the total height) was impregnated in the mixed solution of copper, zinc and aluminum at 50° C. for 1 h. Then, said upper segment was impregnated in a 50° C., 1 mol/L potassium hydroxide solution for 10 min, then washed with water having a conductivity less than 2 µS/cm, until the conductivity of the washing liquid was less than 5 µS/cm; then it was washed with anhydrous ethanol, till the water content in the washing liquid was less than 100 ppm; thereafter, it was dried in a drying oven at 90° C. for 4 h, and calcined in air at 400° C. for 1 h to obtain a one-time impregnation sample. Then, the aforesaid process of mixed solution impregnation-potassium hydroxide solution impregnation-washing-drying-calcination was repeated twice to obtain a catalyst semi-finished product.

31.33 g of copper nitrate, 37.8 g of zinc nitrate and 26.58 g of zirconium nitrate were dissolved in 330 mL of deionized water to prepare a mixed solution of copper, zinc and zirconium. A small amount of nitric acid was added to control the solution to have a pH of 6.5. The lower segment of the above-mentioned coating-containing carrier (¼ of the total height) was impregnated in the mixed solution of copper, zinc and zirconium at 50° C. for 0.5 h. Then, said lower segment was impregnated in a 50° C., 1 mol/L potassium hydroxide solution for 10 min, then washed with water having a conductivity less than 2 µS/cm, until the conductivity of the washing liquid was less than 5 µS/cm; then it was washed with anhydrous ethanol, till the water content in the washing liquid was less than 100 ppm; thereafter, it was dried in a drying oven at 90° C. for 4 h, and calcined in air at 400° C. for 1 h to obtain a one-time impregnation sample. Then, the aforesaid process of mixed solution impregnation-potassium hydroxide solution impregnation-washing-drying-calcination was repeated twice to obtain a monolithic catalyst y24.

Comparative Example 7

188 g of copper nitrate, 113.4 g of zinc nitrate, 42.6 g of aluminum nitrate and 63.8 g of zirconium nitrate were dissolved in 1500 mL of deionized water to obtain a mixed nitrate solution, and the solution was preheated to 65° C.; 1 mol/L sodium carbonate aqueous solution was formulated and preheated to 65° C.; the mixed nitrate solution and sodium carbonate solution were concurrently added to 300 mL of 50° C. deionized water with the pH maintained to 7.2, and then aged in situ for 1 h; the filtration was carried out, and the deionized water having a conductivity less than 2 µS/cm was used for suction filtration and washing of filter cake, until the conductivity of filter liquor was less than 5 S/cm; ethanol was then used for suction filtration and washing, till the water content in the filter cake was less than 100 ppm, thereby obtaining a catalyst precursor; the precursor was dried in a drying oven at 90° C. for 4 h, and calcined in air at 350° C. for 2 h; the resulting powder was tableted and shaped into a cylinder (Φ5 mm×5 mm) to obtain a catalyst C7.

Comparative Example 8

A cylindrical cordierite with a cross-sectional diameter of Φ35 mm, a height of 210 mm and an inner hole diameter of 5 mm was immersed in an aqueous solution of aluminum nitrate and urea in an autoclave for treatment (the amount-of-substance ratio of aluminum nitrate to urea was 3.5, and the amount-of-substance concentration of aluminum nitrate was 1 mol/L) at a pressure of 6 MPa, at a temperature of 80° C. and for a period of 1 h to obtain a precursor of a coating-containing carrier; the precursor was dried in air at 120° C. for 4 h and calcined at 650° C. for 2 h to obtain a coating-containing carrier.

31.33 g of copper nitrate, 15.75 g of zinc nitrate, 10.65 g of aluminum nitrate and 26.58 g of zirconium nitrate were dissolved in 500 mL of deionized water to prepare a mixed solution of copper, zinc, aluminum and zirconium. A small amount of nitric acid was added to control the solution to have a pH of 6.5. The above-mentioned coating-containing carrier was firstly impregnated in the mixed solution of copper, zinc, aluminum and zirconium at 50° C. for 1 h. Then, said coating-containing carrier was impregnated in a 50° C., 1 mol/L potassium hydroxide solution for 10 min, then washed with water having a conductivity less than 2 μS/cm, until the conductivity of the washing liquid was less than 5 μS/cm; then it was washed with anhydrous ethanol, till the water content in the washing liquid was less than 100 ppm; thereafter, it was dried in a drying oven at 90° C. for 4 h, and calcined in air at 400° C. for 1 h to obtain a one-time impregnation sample. Then, the aforesaid process of mixed solution impregnation-potassium hydroxide solution impregnation-washing-drying-calcination was repeated twice to obtain a monolithic catalyst U8.

Activity test conditions: the activity of the catalyst was evaluated on a fixed bed isothermal reactor, and the reaction tube had an inner diameter of 35 mm and a length of 1200 mm. The catalyst was subjected to an in situ reduction in a reactor with a $H_2/N_2$ mixed gas containing 5% $H_2$ before use, and the final temperature of reduction was 240° C. The composition of the feed gas was $CO_2/CO/H_2$=16/13/71 (volume ratio). The reaction pressure was 5 MPa; the space velocity was 10000 $h^{-1}$; and the evaluation temperature was 240° C. After the reaction was stable for 10 h, the sample was determined to result in the initial catalytic performance; then, the feed gas was supplemented by 5% water vapor, and then after stabilization for 10 h, the sample was determined to result in the catalytic performance after the hydrothermal resistance. The product was analyzed by gas chromatography. The evaluation results were shown in Table 1, wherein hydrothermal stability=(initial methanol space-time yield–methanol space-time yield after hydrothermal resistance)/initial methanol space-time yield×100%.

CO and $CO_2$ conversion rates, high methanol space-time yield and good hydrothermal stability.

The invention claimed is:

1. A monolithic catalyst, comprising: a carrier, a coating, a first active component deposited on the coating, and a second active component deposited on the coating, said carrier being a honeycomb ceramic carrier comprising a plurality of holes that extend through the honeycomb ceramic carrier, wherein the coating is applied to a wall of each of the plurality of holes, the honeycomb ceramic carrier is divided into an upper segment and a lower segment in a longitudinal direction, wherein a length of the lower segment is from about ¼ to about ⅘ of a total length of the honeycomb ceramic carrier, wherein the first active component comprises oxides of zinc, aluminum, and optionally copper, and is deposited on the coating on the wall in each hole in the upper segment, and the second active component comprises one or more among bimetallic oxide of Cu—Zn, bimetallic oxide of Ni—Al, polymetallic oxide of Cu—Zn—Zr, and polymetallic oxide Cu—Zn—Al—Zr—Co, and is deposited on the coating on the wall in each hole in the lower segment.

2. The monolithic catalyst according to claim 1 is effective in catalyzing a $CO_2$ hydrogenation reaction.

3. The monolithic catalyst according to claim 1 is effective in catalyzing a $CO_2$-rich syngas hydrogenation reaction.

4. The monolithic catalyst according to claim 1, wherein the honeycomb ceramic is a cylindrical cordierite having a cross-sectional diameter equal to an inner diameter of a

TABLE 4

Catalytic Performance of Catalysts in a reaction of a $CO_2$-enriched syngas for producing methanol

| catalyst | main elemental composition of the upper segment of the inner hole* | main elemental composition of the lower segment of the inner hole* | initial catalytic performance | | | catalytic performance after heat resistance | | | hydrothermal stability/% |
|---|---|---|---|---|---|---|---|---|---|
| | | | CO conversion rate/% | $CO_2$ conversion rate/% | methanol space-time yield/ (g/h/mL) | CO conversion rate/% | $CO_2$ conversion rate/% | methanol space-time yield/ (g/h/mL) | |
| y19 | 25.97% Cu; 7.79% Zn; 12.99% Al. | 32.24% Cu; 5.53% Zn; 17.35% Zr. | 68.1 | 15.2 | 1.61 | 57.9 | 13.1 | 1.38 | 86 |
| y20 | 25% Cu; 12.5% Zn; 10% Al. | 22.18% Cu; 11.09% Zn; 11.15% Zr. | 67.5 | 18.4 | 1.67 | 59.4 | 16.2 | 1.47 | 88 |
| y21 | 22.99% Cu; 18.39% Zn; 6.9% Al. | 20.25% Cu; 15.96% Zn; 9.39% Zr. | 66.1 | 19.3 | 1.67 | 59.5 | 17.4 | 1.51 | 90 |
| y22 | 22.22% Cu; 22.22% Zn; 4.44% Al. | 19.49% Cu; 19.49% Zn; 7.34% Zr. | 65.7 | 20.3 | 1.68 | 59.79 | 18.47 | 1.53 | 91 |
| y23 | 21.5% Cu; 25.8% Zn; 2.15% Al. | 15.6% Cu; 26.74% Zn; 0.65% Zr. | 65.3 | 21.9 | 1.71 | 59.42 | 19.93 | 1.56 | 91 |
| y24 | 26.67% Cu; 13.33% Zn; 8% Al. | 17.21% Cu; 20.65% Zn; 8.1% Zr. | 64.9 | 23.1 | 1.73 | 59.71 | 21.25 | 1.59 | 92 |
| C7 | — | — | 63.9 | 10.1 | 1.42 | 46.65 | 7.37 | 1.04 | 73 |
| U8 | 23.33% Cu; 10.29% Zn; 5.81% Al; 9.68% Zr. | 23.33% Cu; 10.29% Zn; 5.81% Al; 9.68% Zr. | 64.6 | 11.5 | 1.46 | 57.49 | 10.24 | 1.30 | 89 |

*The elemental composition of the active components was determined by the XPS method.

It can be seen from Table 1 that compared with the conventional C catalyst prepared by the co-precipitation and the co-impregnated U catalyst, the monolithic catalyst for producing methanol from the $CO_2$-enriched syngas, as prepared by the process of the present invention, has the high hydrogenation tubular reactor, and a ratio of the length of the honeycomb ceramic to the cross-sectional diameter thereof is from about 1.5 to about 6:1.

5. The monolithic catalyst according to claim 1, wherein the honeycomb ceramic is a cylindrical cordierite, each hole has a cross-sectional shape that is a circle or a square, and a diameter of the circle or a length of a side of the square is from about 1 mm to about 5 mm.

6. The monolithic catalyst according to claim 1, wherein the length of the lower segment is from about ½ to about ¾ of the total length of the honeycomb ceramic carrier.

7. The monolithic catalyst according to claim 1, wherein the coating is $Al_2O_3$ or $\gamma\text{-}Al_2O_3$.

8. The monolithic catalyst according to claim 1, wherein the first active component comprises bimetallic oxide of Zn—Al, polymetallic oxide of Cu—Zn—Al, or both.

9. The monolithic catalyst according to claim 2, wherein the first active component comprises zinc and aluminum, and a molar ratio of zinc to aluminum is (about 0.4-about 0.6):1, and the second active component comprises copper, zinc, aluminum, zirconium, and cobalt, and a molar ratio of copper, zinc, aluminum, zirconium, and cobalt is 1:(about 0.8-about 1.2):(about 0.5-about 1):(about 0.5-about 1.5)):(about 0.1-about 0.8).

10. The monolithic catalyst according to claim 2, wherein the first active component comprises zinc and aluminum, and a molar ratio of zinc to aluminum is (about 0.4-about 0.6):1, and the second active component comprises copper and zinc, and a molar ratio of copper to zinc is (about 0.1-about 0.5):1.

11. The monolithic catalyst according to claim 2, wherein the first active component comprises zinc and aluminum, and a molar ratio of zinc to aluminum is (about 0.4-about 0.6):1, and the second active component comprises nickel and aluminum, and a molar ratio of nickel to aluminum is (about 0.1-about 0.5):1.

12. The monolithic catalyst according to claim 3, wherein the first active component comprises copper, zinc, and aluminum, and a molar ratio of copper, zinc, and aluminum is 100:(about 30-about 120):(about 10-about 50), and the second active component comprises copper, zinc, and zirconium, and a molar ratio of copper, zinc, and zirconium is 100:(about 30-about 120):(about 20-about 100).

13. The monolithic catalyst according to claim 1, wherein the catalyst is placed in a single reactor that is adiabatic or non-adiabatic.

14. A process for preparation of the monolithic catalyst according to claim 1, comprising:
  a. immersing the honeycomb ceramic carrier in a mixed aqueous solution of aluminum nitrate and urea for treatment to obtain a precursor of a coating-containing carrier, and heat-treating the precursor to obtain a coated carrier;
  b. impregnating the upper segment of the coated carrier in solution A, or impregnating the lower segment of the coated carrier in solution B, then contacting the impregnated segment with a first precipitant solution, then after washing, obtaining a catalyst precursor 1, and heat-treating the catalyst precursor 1 to obtain a first catalyst semi-finished product having an untreated lower segment or a second catalyst semi-finished product having an untreated upper segment; and
  c. impregnating the untreated lower segment of the first catalyst semi-finished product in solution B, or impregnating the untreated upper segment of the second catalyst semi-finished product resultant in solution A, then contacting the impregnated lower segment of the first catalyst semi-finished product or the impregnated upper segment of the second catalyst semi-finished product with a second precipitant solution, then after washing, obtaining a catalyst precursor 2, and heat-treating the catalyst precursor 2 to obtain the monolithic catalyst.

15. The process according to claim 14, wherein the impregnation in the preparation step a is carried out in an autoclave at a pressure of from about 0.5 MPa to about 6 MPa, at a temperature of from about 70° C. to about 150° C., for a period of from about 1 h to about 5 h.

16. The process according to claim 14, wherein the heat treatment in the preparation step a comprises firstly drying at about 120° C. for about 4 h, and then calcining at about 600 to about 800° C. for from about 1 h to about 4 h.

17. The process according to claim 14, wherein the solution A is a mixed nitrate solution containing zinc and aluminum, or a mixed nitrate solution containing copper, zinc and aluminum, and the solution B is a mixed nitrate solution containing copper, zinc, aluminum, zirconium, and cobalt, a mixed nitrate solution containing copper and zinc, a mixed nitrate solution containing nickel and aluminum, or a mixed nitrate solution containing copper, zinc and zirconium.

18. The process according to claim 14, wherein the solution A is a mixed nitrate solution containing zinc and aluminum, a pH of the solution A is about 6.0 to about 7.0, a molar ratio of zinc to aluminum is (about 0.4-about 0.6):1, and a total salt molar concentration is from about 0.5 mol/L to about 2 mol/L; and
  the solution B is a mixed nitrate solution containing copper, zinc, aluminum, zirconium and cobalt, a pH of the solution B is about 6.0 to about 7.0, a molar ratio of nitrates of copper, zinc, aluminum, zirconium and cobalt is 1:(about 0.8-about 1.2):(about 0.5-about 1):(about 0.5-about 1.5):(about 0.1-about 0.8), and a total salt molar concentration is from about 0.5 mol/L to about 1 mol/L.

19. The process according to claim 14, wherein the solution A is a mixed nitrate solution containing zinc and aluminum, a pH of the solution A is from about 6.0 to about 7.0, and a molar ratio of zinc to aluminum is (about 0.4-about 0.6):1, a total salt molar concentration is from about 0.5 mol/L to about 2 mol/L; and
  the solution B is a mixed nitrate solution containing copper and zinc, a pH of the solution B is from about 6.0 to about 7.0, a molar ratio of copper to zinc is (about 0.1-about 0.5):1, and a total salt molar concentration is from about 0.5 mol/L to about 1 mol/L.

20. The process according to claim 14, wherein the solution A is a mixed nitrate solution containing zinc and aluminum, a pH of the solution A is from about 6.0 to about 7.0, a molar ratio of zinc to aluminum is (about 0.4-about 0.6):1, a total salt molar concentration is from about 0.5 mol/L to about 2 mol/L; and
  the solution B is a mixed nitrate solution containing nickel and aluminum, a pH of the solution B is from about 6.0 to about 7.0, a molar ratio of nickel to aluminum is (about 0.1-about 0.5):1, and a total salt molar concentration is from about 0.5 mol/L to about 1 mol/L.

21. The process according to claim 14, wherein the solution A is a mixed nitrate solution containing copper, zinc, and aluminum, a pH of the solution A is from about 6.0 to about 7.0, a molar ratio of copper, zinc, and aluminum is 100:(about 30-about 120):(about 10-about 50), and a total salt molar concentration is from about 0.5 mol/L to about 2 mol/L; and the solution B is a mixed nitrate solution containing copper, zinc, and zirconium, a pH of the solution B is from about 6.0 to about 7.0, a molar ratio of copper, zinc, and zirconium is 100:(about 30-about 120):(about 20-about 100), and a total salt molar concentration is from about 0.5 mol/L to about 2 mol/L.

22. The process according to claim 14, wherein the first precipitant solution or the second precipitant solution comprises one or more precipitant selected from the group consisting of sodium carbonate, sodium hydrogencarbonate, sodium hydroxide, potassium carbonate, potassium hydrogencarbonate, and potassium hydroxide.

23. The process according to claim 14, wherein the impregnation in the solution A or the solution B in the preparation step b or c is carried out at a temperature from about 30° C. to about 80° C. for about 0.5 h to about 8 h.

24. The process according to claim 14, wherein the washing in the preparation step b or c comprises firstly washing with water having a conductivity of less than 2 μS/cm until the washing liquid has a conductivity less than 5 μS/cm; and washing with anhydrous ethanol until the washing liquid has a water content less than 100 ppm.

25. The process according to claim 18, wherein the heat treatment in the preparation step b or c comprises firstly drying at about 90° C. for about 4 h, and then calcining at a temperature of from about 500° C. to about 800° C. for from about 0.5 h to about 4 h.

26. The process according to claim 21, wherein the heat treatment in the preparation step b or c comprises firstly drying at about 90° C. for about 4 h, and then calcining at a temperature of about 300° C. to about 500° C. for from about 0.5 h to about 4 h.

27. The process according to claim 14, wherein a length of the lower segment is from about ½ to about ¾, of the total length of the monolithic catalyst.

* * * * *